(12) United States Patent
Larson et al.

(10) Patent No.: US 11,607,205 B2
(45) Date of Patent: Mar. 21, 2023

(54) BIOPSY SYSTEM FOR ENHANCED TISSUE HARVESTING

(71) Applicants: ARIZONA BOARD OF REGENTS ON BEHALF OF THE UNIVERSITY OF ARIZONA, Tucson, AZ (US); BANNER UNIVERSITY MEDICAL GROUP, Phoenix, AZ (US); DATA DRIVEN DIAGNOSTIC SCIENCES, INC., Tucson, AZ (US)

(72) Inventors: Michael C. Larson, Tucson, AZ (US); Charles T. Hennemeyer, Tucson, AZ (US)

(73) Assignees: ARIZONA BOARD OF REGENTS ON BEHALF OF THE UNIVERSITY OF ARIZONA, Tucson, AZ (US); BANNER UNIVERSITY MEDICAL GROUP, Phoenix, AZ (US); DATA DRIVEN DIAGNOSTIC SCIENCES, INC., Tucson, AZ (US)

( * ) Notice: Subject to any disclaimer, the term of this patent is extended or adjusted under 35 U.S.C. 154(b) by 678 days.

(21) Appl. No.: 16/559,402

(22) Filed: Sep. 3, 2019

(65) Prior Publication Data

US 2019/0388073 A1 Dec. 26, 2019

Related U.S. Application Data

(63) Continuation-in-part of application No. PCT/US2018/020851, filed on Mar. 5, 2018.
(Continued)

(51) Int. Cl.
*A61B 10/02* (2006.01)
*A61B 18/00* (2006.01)

(52) U.S. Cl.
CPC .......... *A61B 10/0275* (2013.01); *A61B 10/02* (2013.01); *A61B 10/0283* (2013.01);
(Continued)

(58) Field of Classification Search
CPC . A61B 10/0275; A61B 10/02; A61B 10/0283; A61B 2010/0208;
(Continued)

(56) References Cited

U.S. PATENT DOCUMENTS 5,250,065 A * 10/1993 Clement .................. A61M 1/84
606/160
5,335,671 A * 8/1994 Clement ........ A61B 17/320016
600/566
(Continued)

FOREIGN PATENT DOCUMENTS

EP 2726144 B1 2/2016
EP 2726144 B1 10/2016
(Continued)

OTHER PUBLICATIONS

International Search Report Issued For PCT Application No. PCT/US2018/020851 dated May 16, 2018.
(Continued)

*Primary Examiner* — Sean P Dougherty
(74) *Attorney, Agent, or Firm* — Nguyen Tarbet LLC

(57) ABSTRACT

A biopsy system for harvesting larger volumes of tissue as compared to standard core biopsy needles. The system has a needle with a lumen, an aperture disposed at the distal end of the needle and connected to the lumen, and a cutting mechanism adapted to cut tissue. When the needle is rotated after it is inserted into a target tissue, the cutting mechanism cuts from the tissue and directs the cut tissue portions into
(Continued)

the lumen. Multi-bioimpedance measurements are used to guide a needle and direct the application of electricity for cauterizing tissue.

20 Claims, 22 Drawing Sheets

Related U.S. Application Data

(60) Provisional application No. 62/466,549, filed on Mar. 3, 2017.

(52) U.S. Cl.
CPC ........... *A61B 2010/0208* (2013.01); *A61B 2010/0225* (2013.01); *A61B 2018/00577* (2013.01); *A61B 2018/00595* (2013.01)

(58) Field of Classification Search
CPC .. A61B 2010/0225; A61B 2018/00577; A61B 2018/00595; A61B 10/0266
See application file for complete search history.

(56) References Cited

U.S. PATENT DOCUMENTS

| | | | |
|---|---|---|---|
| 5,435,805 A * | 7/1995 | Edwards | A61B 18/1442 604/22 |
| 5,470,308 A * | 11/1995 | Edwards | A61B 18/1815 604/22 |
| 5,505,210 A * | 4/1996 | Clement | A61B 17/3203 600/566 |
| 5,882,316 A | 3/1999 | Chu et al. | |
| 6,022,362 A * | 2/2000 | Lee | A61B 10/0266 600/564 |
| 6,306,132 B1 * | 10/2001 | Moorman | A61B 18/18 606/41 |
| 8,175,679 B2 | 5/2012 | Gerhart et al. | |
| 8,473,029 B2 | 6/2013 | Gerhart et al. | |
| 10,695,037 B2 | 6/2020 | Vetter et al. | |
| 10,835,312 B2 | 11/2020 | Vetter | |
| 2002/0026188 A1 | 2/2002 | Balbierz et al. | |
| 2002/0049442 A1 | 4/2002 | Roberts et al. | |
| 2002/0072688 A1 | 6/2002 | Burbank et al. | |
| 2002/0077648 A1 | 6/2002 | Lee et al. | |
| 2002/0099398 A1 * | 7/2002 | Lee | A61B 17/320725 606/159 |
| 2002/0099399 A1 | 7/2002 | Lee et al. | |
| 2002/0123762 A1 * | 9/2002 | Lee | A61B 8/085 606/159 |
| 2003/0109802 A1 | 6/2003 | Laeseke et al. | |
| 2003/0163128 A1 | 8/2003 | Patil et al. | |
| 2003/0229292 A1 * | 12/2003 | Hibner | A61B 10/0275 600/566 |
| 2004/0176789 A1 * | 9/2004 | Lee | A61B 10/0266 606/167 |
| 2006/0015035 A1 | 1/2006 | Rock | |
| 2010/0324446 A1 | 12/2010 | Pendleton | |
| 2010/0331883 A1 * | 12/2010 | Schmitz | A61B 17/0218 606/279 |
| 2014/0066922 A1 | 3/2014 | Coe et al. | |
| 2015/0038872 A1 | 2/2015 | Halter | |
| 2015/0223718 A1 * | 8/2015 | Nambu | A61B 18/1477 607/45 |
| 2015/0265751 A1 * | 9/2015 | Ivorra Cano | F16B 12/00 600/567 |
| 2016/0029920 A1 | 2/2016 | Kronström et al. | |
| 2016/0058433 A1 | 3/2016 | Burbank et al. | |
| 2016/0317212 A1 * | 11/2016 | Ge | A61B 18/148 |
| 2017/0273671 A1 * | 9/2017 | Reich | A61B 10/0275 |
| 2018/0140289 A1 * | 5/2018 | Benning | A61B 10/06 |
| 2018/0296197 A1 | 10/2018 | Kronström et al. | |
| 2021/0361267 A1 * | 11/2021 | Benning | A61B 10/0266 |

FOREIGN PATENT DOCUMENTS

| | | | | |
|---|---|---|---|---|
| EP | 2978370 B1 | 5/2019 | | |
| WO | WO-0182998 A2 * | 11/2001 | ......... | A61B 10/0266 |
| WO | WO-2005079682 A1 * | 9/2005 | ..... | A61B 17/320016 |
| WO | 2009085487 A1 | 7/2009 | | |
| WO | 2013001510 A1 | 1/2013 | | |
| WO | WO-2013076439 A1 * | 5/2013 | ............ | A61B 18/14 |
| WO | 2014155282 A1 | 10/2014 | | |
| WO | 2016198910 A1 | 12/2016 | | |
| WO | 2018015782 A1 | 1/2018 | | |
| WO | 2018161067 A1 | 7/2018 | | |
| WO | 2018161067 A1 | 9/2018 | | |

OTHER PUBLICATIONS

Loh et al. "Comparative healing of surgical incisions created by the PEAK PlasmaBlade, conventional electrosurgery, and a scalpel", Plast Reconstr Surg, Dec. 2009,124(6):1849-59.

* cited by examiner

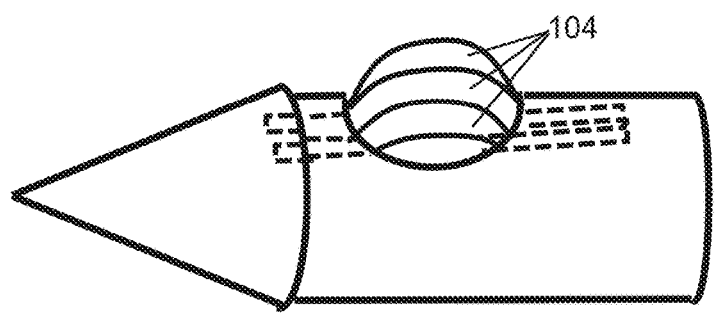
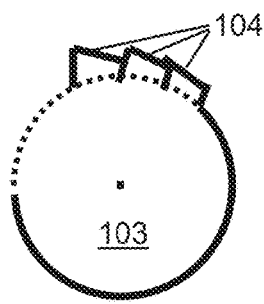
FIG. 3A         FIG. 3B
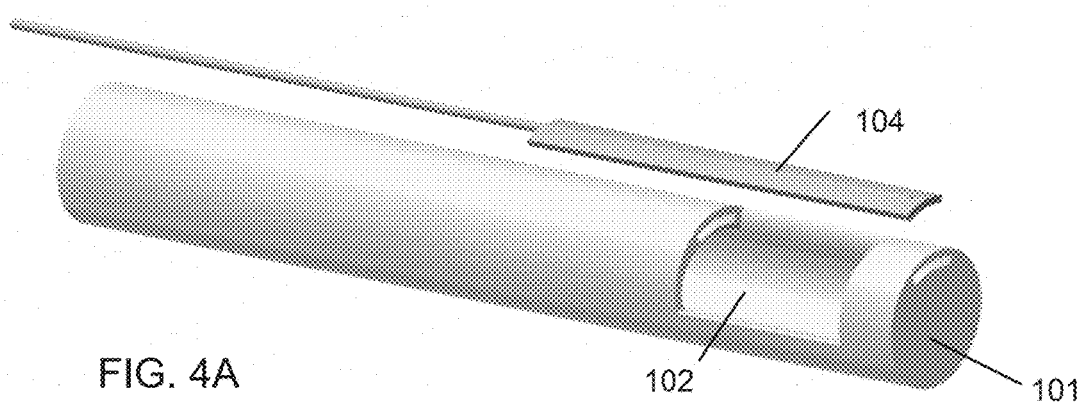
FIG. 4A
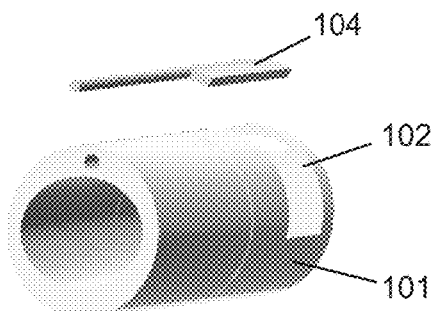
FIG. 4B
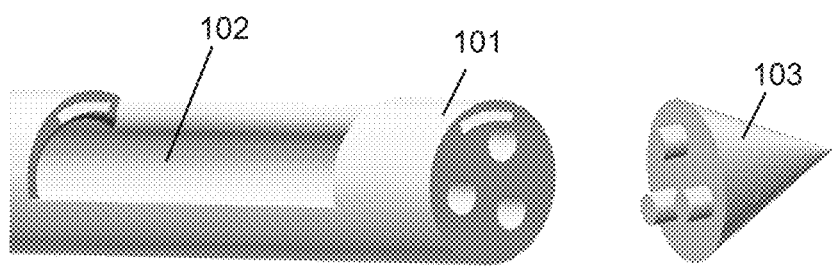
FIG. 5

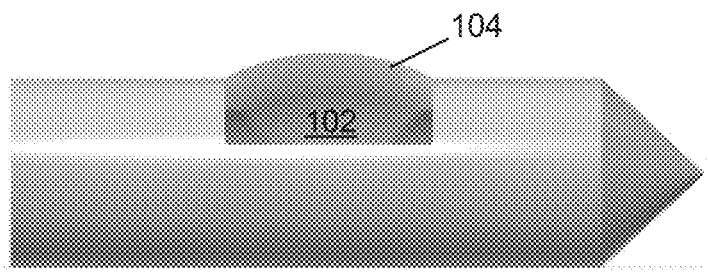
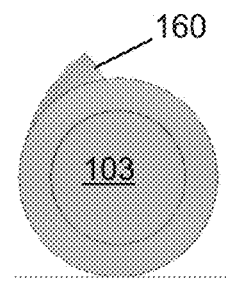
FIG. 6A
FIG. 6B
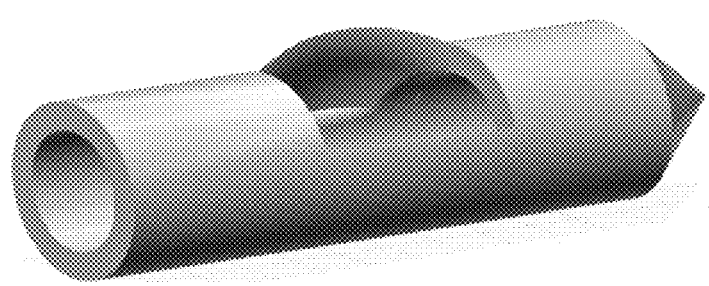
FIG. 6C
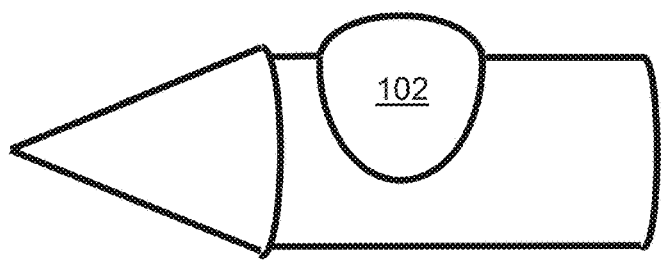
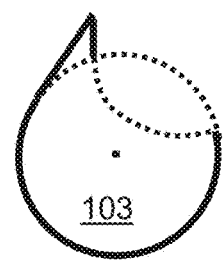
FIG. 6D
FIG. 6E
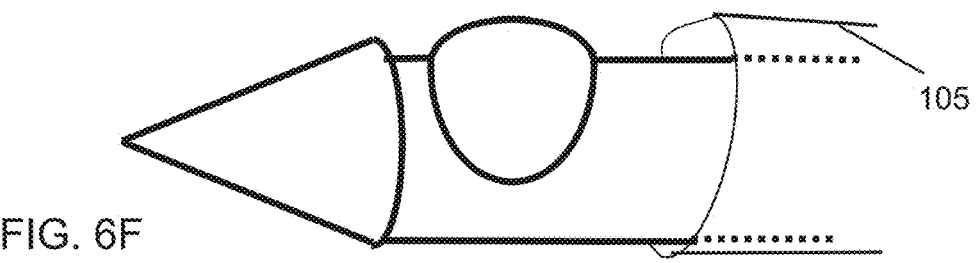
FIG. 6F
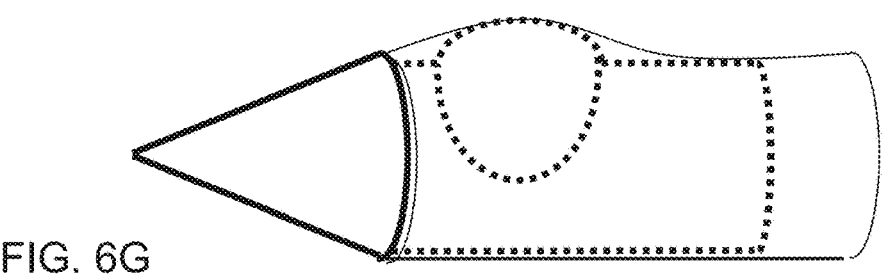
FIG. 6G FIG. 7A
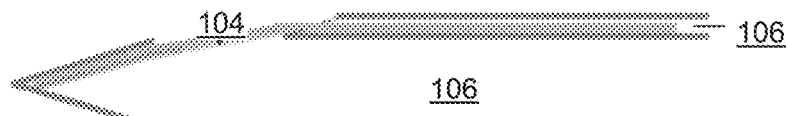
FIG. 7B
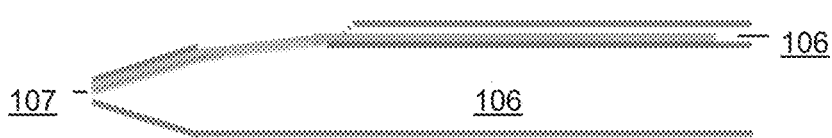
FIG. 7C
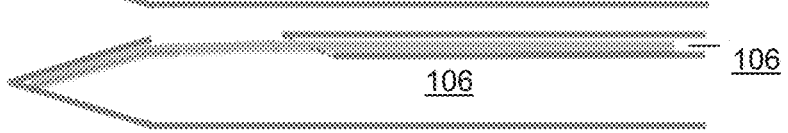
FIG. 7D  FIG. 7E
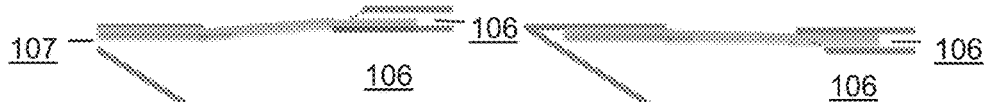
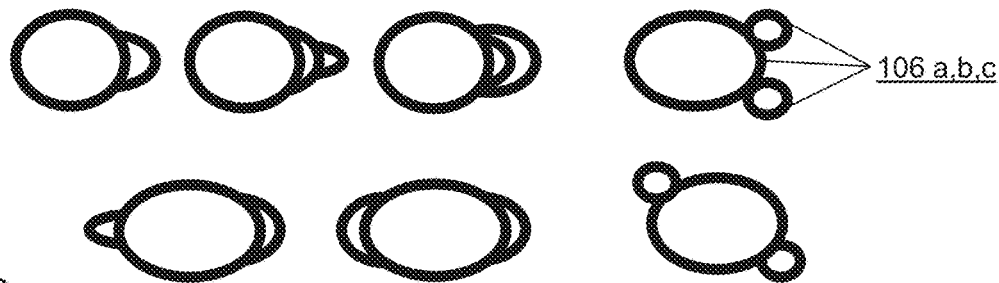
FIG. 8
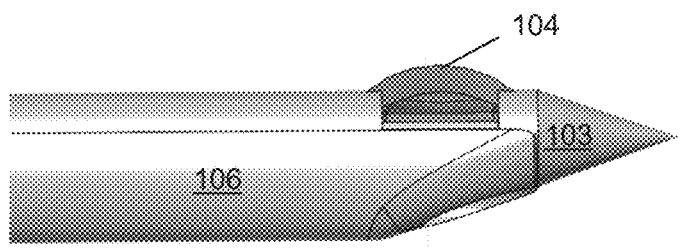  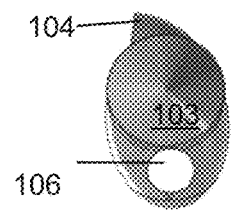
FIG. 9A  FIG. 9B
FIG. 9C

Volume=$2\pi R \times \pi r^2 \times n$
R is the needle sweep radius
r is the cut tissue radius
n is the number of turns

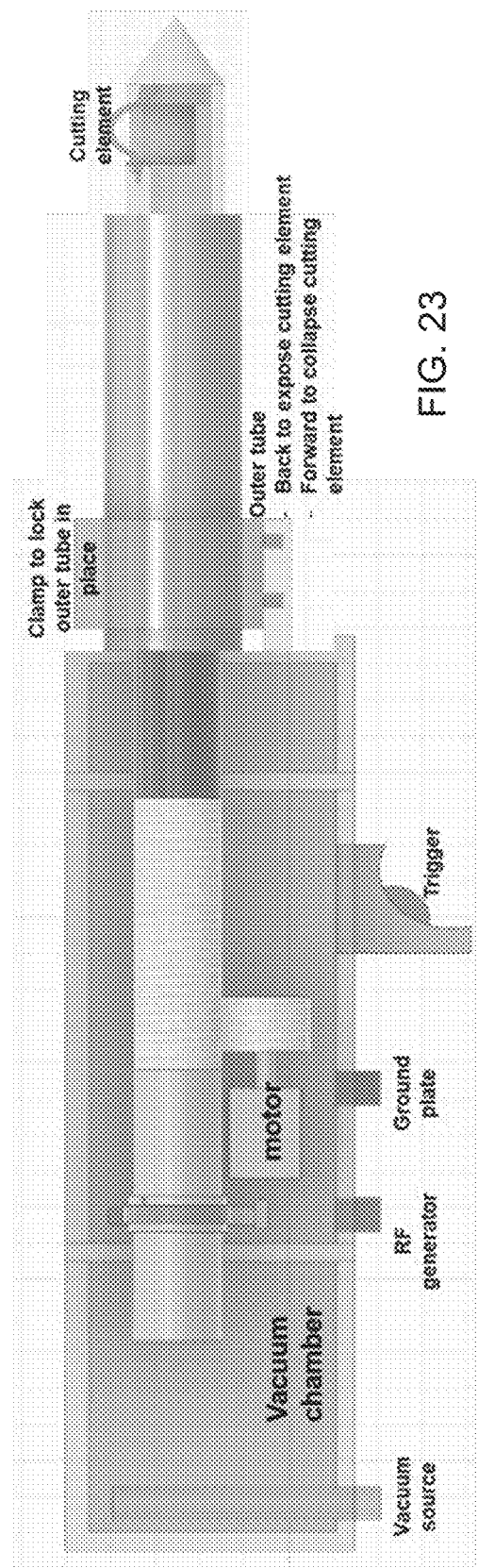
FIG. 23
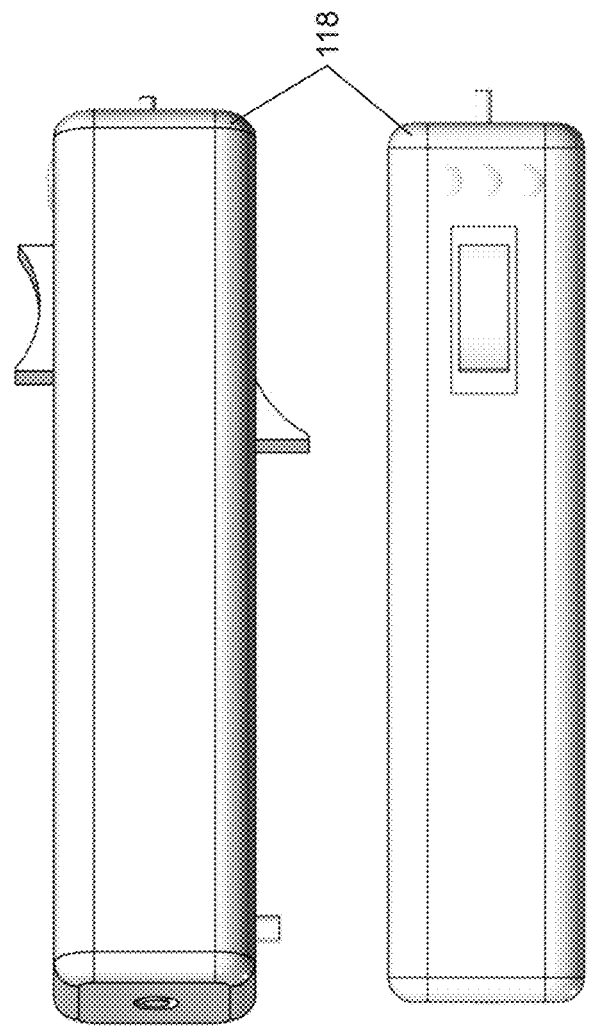
FIG. 24A
FIG. 24B

BIOPSY SYSTEM FOR ENHANCED TISSUE HARVESTING

CROSS REFERENCE

This application is a continuation-in-part and claims benefit of PCT/US2018/020851 filed Mar. 5, 2018, which claims benefit of U.S. Patent Application No. 62/466,549 filed Mar. 3, 2017, the specification(s) of which is/are incorporated herein in their entirety by reference.

FIELD OF THE INVENTION

The present invention relates to devices and methods for performing biopsies, more particularly, to a biopsy system featuring a deployable mechanism for cutting biopsy samples and cauterization. The present invention further provides multi-bioimpedance measurements for guiding a needle and directing electrical coagulation.

BACKGROUND OF THE INVENTION

In patients suspected of having a disease with potentially harmful treatments, such as cancer, a small sample of tissue, termed a biopsy, is needed to make a correct diagnosis. In some cases, a biopsy is used to identify specific cancer characteristics to allow for a more personalized therapy. Large amounts of tissue (e.g., up to one gram) often need to be harvested in order to perform diagnostic and specialized testing (e.g., immunohistochemistry, molecular and genetic testing, etc.). Currently, standard core needle biopsies require multiple passes through tissue to collect enough tissue cores (e.g., cylinders of tissue dictated by the radius of the needle and the height of the core). However, more passes by the needle increases the likelihood of complications such as bleeding or even death. In addition, an increased number of passes may mean longer procedural times and longer post-procedural monitoring. Another means of obtaining more tissue is the use of a larger needle, but bigger needles also carry increased risk of complications, such as bleeding or other organ-specific complication (e.g. pneumothorax, etc).

In another aspect, guidance of needles (hollow in the case of aspiration, partially or semi-hollow in the case of biopsies, or solid as with thermal- or electrical-ablations) is essentially required to maximize efficacy and minimize complications of percutaneous needle-based procedures. While the current standard of external imaging-based guidance through, for example, x-rays/fluoroscopically/CT, medical ultrasound, or MRI, is very powerful, there are limitations. As an example, CT-guidance for lung biopsies is fraught with difficulties. Patients undergoing lung biopsy are often instructed to hold their breath while a CT scan is performed to determine if the trajectory of the needle is in line with the target lesion. However, many patients cannot reasonably hold their breath for the duration of the scan, let alone the brief time for interpretation of the scan including triangulating the trajectory of the needle and the target and then the time it takes for appropriate advancement of the needle to the target. During this interval from scan to needle advancement to the target, the needle tip moves with respirations and lung movement. Furthermore, despite the most proficient percutaneous intervention, complications related to bleeding do occur from the needle violating blood vessels.

Hence, there exists a need for safer and more efficient biopsy needles and procedures. In addition, better guidance and positioning of needles is desired.

SUMMARY OF THE INVENTION

In some aspects, the present invention features a biopsy system for harvesting a target tissue. The system may comprise a needle having a tip disposed at a distal end of the needle for insertion into tissue, a lumen disposed in the needle, an aperture disposed at or near the distal end of the needle and fluidly connected to the lumen, a cutting mechanism adapted to cut tissue, a mechanism for cauterizing contacting tissue, and a mechanism for rotating the needle. The cutting mechanism can have at least a portion thereof disposed in or on the aperture. In one embodiment, the cutting mechanism and aperture may be disposed on the needle shaft near the distal end. In preferred embodiments, when cutting the tissue, the cutting mechanism cuts tissue tangential to the biopsy needle shaft. As used herein, "tangential'" refers to being located at a periphery or side of the needle shaft, but excluding the distal end such that the cutting mechanism does not cut along the axis of the needle. In other preferred embodiments, the cutting mechanism cuts the tissue and directs said cut tissue into the aperture and further into the lumen, while the contacting tissue is cauterized by the cauterizing mechanism. The biopsy system is adapted to cut tissue and harvest said tissue sample (in a corkscrew configuration) into the lumen. For example, the tissue that is being cut acquires a coil shape. As used herein, "contacting tissue" refers to the remaining tissue from which was harvested the cut tissue sample and that is in contact with the cauterizing mechanism.

In some embodiments, the cutting mechanism may be deployable such that it is adapted to move between an extended position where said portion projects from the needle, and a retracted position where said portion is not projecting from the aperture. When the needle, starting with the tip, is inserted into the target tissue, the cutting mechanism moves to the extended position and the needle is axially rotated via the rotation mechanism. In some embodiments, the system may further comprise a sheath slidably disposed around an exterior surface of the needle. The sheath is adapted to move between at least an open position where the aperture is exposed and the sheath is moved towards the proximal end of the needle, and a closed position where the aperture is covered by the sheath. When the sheath is moved to the open position, the deployable cutting mechanism expands and projects out from the aperture. In some embodiments, the deployable cutting mechanism may comprise at least one cylindrical or filament wire or an expandable dome-shape structure. In other embodiments, the deployable cutting mechanism comprises at least one flat wire with a first side for cutting and a second side for cauterization or coagulation. In still other embodiments, the deployable cutting mechanism may comprise a nitinol memory wire that is pre-configured to assume a conformation.

According to one embodiment, the biopsy system of the present invention may have a fixed-shaped cutting mechanism instead of the deployable cutting mechanism. As used herein, the term "fixed-shaped" is defined as non-deployable. This fixed-shaped cutting mechanism may extend from the needle. For example, the fixed cutting mechanism may be disposed at the aperture and extend from the needle surface. The sheath may be adapted to move between at least an open position where the aperture and cutting mechanism are exposed and a closed position where the aperture and cutting mechanism are covered by the sheath. In some embodiments, the cutting mechanism may comprise a fixed dome-shape structure having a leading cutting edge.

According to some embodiments, the biopsy system may further comprise a means for retracting the sheath to move between the open position and the closed position. For instance, a gear may be operatively coupled to the sheath and a motor for moving the sheath between the open position and the closed position. The gear may be operatively coupled to the sheath via a posterior connection. Alternatively, the gear may be operatively coupled to the sheath via a gear track disposed on an exterior surface of the sheath.

According to some embodiments, the rotating mechanism may comprise a gear operatively coupled to the needle and to a spring or motor for rotating the needle. The gear may be operatively coupled to the spring or motor via a rod or other connection capable of transferring rotational force. In other embodiments, the system may have at least two gear systems, where one gear set controls the sheath retraction and the other gear set controls the needle rotation. Alternatively, the system may have one or more gears that can simultaneously control the sheath retraction and needle rotation.

In some embodiments, the lumen is under negative pressure to allow the cut tissue to collect in the lumen. The negative pressure in the lumen can be generated using suction or a vacuum source. In other embodiments, a tissue collection chamber may be fluidly coupled to the needle lumen for storing the cut tissue. For example, suction may be applied to help withdraw the tissue into the lumen, which is then stored in the collection chamber.

According to one embodiment, the cauterizing mechanism may be operatively connected to the cutting mechanism, which is an electrocautery system. When the electrocautery system is activated, the cutting mechanism is activated to provide cauterization to contacting tissue. According to another embodiment, the cauterizing mechanism may comprise a cauterizing surface disposed on the cutting mechanism such that the cauterizing surface cauterizes the contacting tissue. In another embodiment, the cauterizing mechanism may comprise a cauterizing surface disposed on the needle tip such that the cauterizing surface cauterizes the contacting tissue. For example, the cauterizing surface of the needle tip can act as an exposed anode, and a shaft of the needle can act as a cathode. In other embodiments, the cauterizing mechanism may further comprise an insulator that protects the cut tissue from being cauterized. The cauterizing mechanism can be operatively coupled to a power source, such as a battery, power outlet, or any suitable electrical source.

In one embodiment, the cutting mechanism may utilize cutting, electromagnetic force, pressure, thermal energy, vibrational energy, or a combination thereof to cut the tissue. In other embodiments, the cutting mechanism may utilize high frequency electrical pulses to cut the tissue with minimal burning or damaging of the tissue.

In further embodiments, the biopsy system may include at least one additional lumen. In some embodiments, the lumen may have a cross section that is circular shaped, oval shaped, semicircular shaped, sectoral shaped, pie- or arc-shaped, rectangular shaped, elliptical shaped, teardrop-shaped, crescent-shaped, horseshoe-shaped, triangular shaped, square shaped, polygonal shaped, or a combination thereof. In other embodiments, the lumen is symmetric, oblong, or asymmetric relative to an axis of expansion or rotation. In one embodiment, the additional lumen is adapted for holding or administering a solution. The solution may be injectable into the tissue. For example, the solution may comprise a procoagulant, local anesthetic, or other injected medication desired by the operator.

In other embodiments, the tip of the needle is hollow, beveled, solid, or tapered. In some other embodiments, the tip of the needle may comprise symmetrical or asymmetrical conical tips, or other configurations. In yet other embodiments, the tip of the needle comprises a cutting edge or a reverse cutting edge.

In one embodiment, the tip or cutting mechanism may be removed from the needle. Without wishing to limit the present invention, the removed tip or cutting mechanism may function as a tissue biopsy marker or wire localizer for indicating a location of the biopsied tissue. In another embodiment, the needle lumen or the additional lumen may also be used for the insertion or withdrawal of a guide wire and/or the insertion of a radio-opaque marker.

In yet other embodiments, the biopsy system may further a mechanism for transmitting signals that enables a user to better visualize and locate the needle in the tissue. For example, the mechanism may emit signals that are ultrasonic vibrations. These ultrasonic vibrations can then be detected by an ultrasound machine.

According to preferred embodiments, the biopsy systems described herein may be employed in biopsy procedures. For example, in some embodiments, the biopsy procedure, or method of harvesting tissue, may comprise providing the biopsy system, inserting the needle, starting with the tip, into a tissue of concern, retracting the sheath to expose the cutting mechanism, rotating the needle and applying suction to the lumen, thereby cutting the tissue with the cutting mechanism and cauterizing contacting tissue via the cauterizing mechanism. The cut tissue is then directed into the lumen and optionally stored in the tissue collection chamber. In some embodiment, the method may further comprise injecting a solution, such as, for example, a medication into the tissue, through an additional lumen. In other embodiments, the cutting mechanism delivers vibrational, thermal, or electrical energy to assist in locating the needle in the tissue under image-guidance. In still other embodiments, the method may further comprise removing the tip (103) or cutting mechanism (104) from the needle and placing the removed tip or cutting mechanism in the biopsied tissue.

According to other embodiments, the present invention features a bio-impedance system for guiding a needle and providing positioning information. In some aspects, the system may comprise a needle having a tip disposed at a distal end of the needle for insertion into tissue, an outer sheath slidably disposed around an exterior surface of the needle, and a plurality of electrodes disposed on a surface of the outer sheath, on the needle, or both. The outer sheath is adapted to move between an open position away from the needle tip such that at least a portion of the needle is exposed, and a closed position where said needle portion is covered by the sheath. In one embodiment, the needle can function as an additional electrode. Each electrode is configured to apply electrical current to the immediate surroundings in contact with the electrode to achieve one or more of the following results: cauterizing tissue, coagulating blood, obtaining multiple bio-impedance measurements to guide needle insertion and positioning, or initiating electron-dependent biochemical processes.

In some embodiments, the plurality of electrodes may comprise about 3-128 electrodes that are electrically capable yet isolatable from the other electrodes. In one embodiment, the electrodes may comprise conductive strips, ribbons, or wires disposed axially along the surface of the outer sheath, the needle surface, or embedded and fixed within the needle. In another embodiment, the electrodes may comprise multiple concentric telescoping tubes each with an electrically-active exposed tip. In some embodiments, an insulating material may be partially covering the electrodes, a portion of the needle, or both.

In some embodiments, the needle may be hollow, partially hollow, or solid with more than one face that conducts electricity. In other embodiments, the contents inside the needle, such as saline or a wire disposed in the needle, are electrically conductive and may serve as additional electrode(s). In some other embodiments, the needle may have one or more electrically capable and isolatable connection disposed internally. In some embodiments, the needle may be circular or non-circular in cross-section. In one aspect, non-circular faces may improve diagnostic ultrasound guidance and/or enable alternative manufacturing.

One of the unique and inventive features of the present invention is the deployable cutting mechanism (e.g., filament or wire) with cauterization. Without wishing to limit the invention to a particular theory or mechanism, the present invention can harvest larger volumes of tissue as compared to standard core biopsy needles. This may help reduce the number of passes that are performed during a biopsy, thus potentially reducing biopsy-associated complications and procedure time. Furthermore, the system can harvest the tissues while cauterizing the contacting tissue (e.g. remaining tissue), which can also reduce biopsy-associated complications.

Another unique and inventive feature of the present invention is the multiple electrodes on the biopsy needle. This enables more than one impedance measurement to be obtained for providing spatial information. Without wishing to limit the invention to a particular theory or mechanism, this feature can allow for guided insertion of the biopsy needle using directional information from multiple bio-impedance readings by the electrodes, thereby further reducing the likelihood of biopsy-associated complications. None of the presently known prior references or works has these unique inventive technical features of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIGS. 3A-3B show an alternative embodiment of the biopsy needle device where the cutting element comprises a multitude of filaments used instead of a single filamentous ribbon or wire. Again, dashed lines represent elements hidden from direct view.

FIGS. 4A-4B show an alternative embodiment of the biopsy needle device where the filament may run inside the hollow needle in its entirety.

FIG. 5 shows the biopsy needle device with the cone tip inserted on the end of the hollow needle.

FIGS. 6A-6G show an alternative embodiment of the cutting element comprising a cutting dome, which may enable rotational cutting beyond the confines of a needle. Dashed lines represent objects hidden from view.

FIGS. 7A-7E show cut-away longitudinal side views of additional possible tip geometries and expanding/cutting mechanisms, with different orientations of the main lumen, secondary lumen, and needle tip.

FIG. 8 is of cross-section views of other possible multiple lumen geometries when looking down the bore(s).

FIGS. 9A-9C show an alternative embodiment of the biopsy needle device with a dual-lumen, cutting dome configuration.

FIG. 23 shows another non-limiting embodiment of the biopsy needle system.

FIGS. 24A-24B show alternative embodiments of an encasement/handle of the biopsy needle system.

DETAILED DESCRIPTION OF THE INVENTION

Figure 1A:
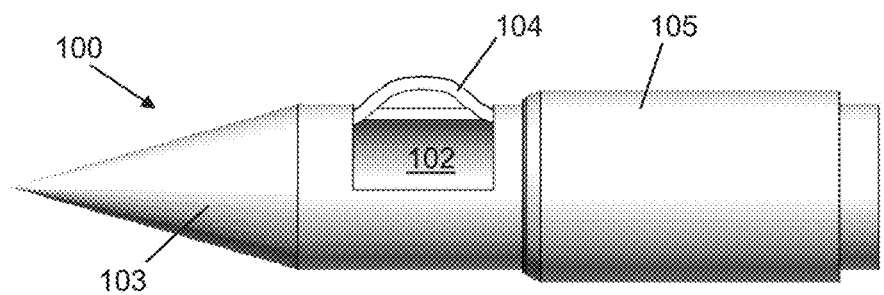
FIGS. 1A-1D show a non-limiting embodiment of a biopsy needle device of the present invention in side (FIG. 1A, 1C) and front views (FIG. 1B, 1D). In one embodiment, the biopsy needle device may comprise a hollow needle with an aperture near the distal end, a sharp conical tip affixed to a cutting element, and a retractable movable sheath.

Following is a list of elements corresponding to a particular element referred to herein:
100 biopsy needle system
101 needle
102 aperture
103 needle tip
104 cutting element
105 sheath
106 lumen
107 localizing wire hole
108 back port
109 side port
110 posterior connection
111 posterior opening
112 rotational connection
113 gear
114 seal
115 vacuum collection chamber
116 attachment
117 syringe
118 encasement
119 translation spring
120 spring switch
121 spring dial
122 rotational spring
123 rod with gear
124 toothed rod and gear
125 trigger
126 safety switch
127 plunger
128 one-way valve
129 syringe lock
130 battery
131 button
132 electrical connection
133 Luer lock
160 cutting edge
161 cauterization surface
162 dielectric/insulating component
164 electrode As known to one of ordinary skill it the art, cauterization involves burning or singeing a target tissue typically to coagulate and stop bleeding and reduce or prevent infections. The cauterized area then heals.

As used herein, the term "electrocautery" refers to cauterization, preferably without significant tissue damage. In some embodiments, electrocautery applies high frequency alternating current by a unipolar or bipolar method. The high frequency alternating current may be applied intermittently to coagulate tissue. As used herein, the term "electrosurgery" refers to pulsating at higher frequencies to cut with little thermal damage. The high frequency alternating current may be applied in a continuous waveform to cut tissue. In some embodiments, this is the preferred method for cutting using the biopsy needle device of the present invention. The biopsy device may be operatively connected to an electrical generator or power source for cauterization and/or surgical cutting. In one embodiment, an example of the electrosurgical and/or electrocautery unit that may be used in accordance with the present invention include a unipolar unit with one polarity on or near the cutting element and a second polarity placed on the patient using an electrode pad and connected to the electrical unit/generator. In another embodiment, the electrosurgical and/or electrocautery may comprise a bipolar unit with one polarity on or near the cutting element and a second polarity placed on another part of the needle device within the patient. In preferred embodiments, the unit is capable of both cutting and coagulating the tissue.

As known to one of ordinary skill, bio-impedance is the measurement of resistance to alternating current flow in a biological organism or specimen. Bio-impedance can be used to provide information to a healthcare provider such as, for example, placement of a needle in the desired tissue given that the electrical conductivity of different tissue types is variable.

Biopsy Needle

According to some embodiments, the present invention features a biopsy system (100) for collecting biopsy samples. The biopsy system (100) of the present invention comprises a needle (101) (e.g., a hollow shaft, a partially hollow shaft, a multi-lumened shaft, etc.) having a distal end, i.e. needle tip, for insertion into tissue under investigation and a proximal end opposite the distal end. The distal end may be pointed or tapered or configured in any appropriate shape for insertion into tissue under investigation. In some embodiments, the needle gauge may range from about 8-30 gauge. In other embodiments, the tip angle of the needle may range from about 0°-45°. The needle may be constructed from a stainless steel, other metal, or ceramic material; and may optionally be coated for insulation. In some embodiments, the needle surfaces are flat to increase echogenicity.

An aperture or opening aperture (102) may be disposed in the needle at or near the distal end. A sheath (105) may be disposed (e.g., slidably disposed, rotatably disposed, movably disposed) on and/or around at least a portion of the needle, e.g., over at least a portion of the aperture (102). The aperture (102) can be exposed if not covered by the sheath (105). For example, the sheath (105) can move between at least an open position wherein the aperture (102) is exposed and a closed position wherein the aperture (102) is covered. The aperture (102) may be used to house a (deployable) cutting mechanism for cutting tissue (as described below). During the cutting process, cut tissue may be directed from the originating tissue or mass into the needle (e.g., a lumen (106) in the needle) via the aperture (102). The system (100) may feature a single lumen (106) or multiple lumens (106), e.g., two, three, four, five, six, more than six, etc. In some embodiments, tissue may be aspirated or harvested into one lumen and a solution may be present in a second lumen.

The system (100) of the present invention also comprises a (deployable) cutting mechanism (104) for cutting tissue. The deployable cutting mechanism (104) may also cauterize tissue. In some embodiments, the deployable cutting mechanism (104), e.g., the cutting portion, is extendable from the aperture (102). The remaining portion of the deployable cutting mechanism (104) may optionally extend through at least a portion of the needle from the aperture (102), e.g., extend toward the proximal end of the needle. In some preferred embodiments, the proximal and distal ends of the cutting mechanism are secured and supported to stabilize the cutting element against improper movement. The present invention is not limited to this configuration. In some embodiments, when the sheath (105) is moved to the open position, the deployable cutting mechanism (104) extends (e.g., pops out from, is forced out from, etc.) from the aperture (102) into the surrounding tissue. Preferably, the inner diameter of the sheath may be sufficiently large to fit around the needle and allow for movement of the sheath about the needle, while also being sufficiently fitted to secure the cutting mechanism in a non-expanded configuration when the sheath is in the closed position. The length of the sheath may be shorter than the length of the needle to allow for movement of the sheath between the closed and open position to expose the cutting mechanism.

In some embodiments, the deployable cutting mechanism (104) may be any appropriate component for surgical cutting (and optionally cauterizing) tissue to allow for tissue harvesting. In some embodiments, the deployable cutting mechanism (104) may comprise one or more wires or filaments. In other embodiments, the deployable cutting mechanism (104) may comprise one or more strips, e.g., a flat wire or flat shaft with side edges, e.g., one side edge is sharp for cutting, one side edge is a coagulating edge, etc. In some embodiments, a portion of the deployable cutting mechanism (104) functions as an insulator to help protect the tissue being harvested from the cauterization or burning. For example, one side edge of the deployable cutting mechanism (104) may be for cauterizing and the other side edge may be for cutting. In some embodiments, the deployable cutting mechanism (104) has features to allow for controlled deployment, e.g., notches, etc.

In some embodiments, the cutting mechanism (104) may not necessarily be a component that deploys or pops out of the aperture (120). For example, in some embodiments, the cutting mechanism (104) may comprise nitinol wire (memory wire) or a component that may make suction less necessary (e.g., like a scoop). In other embodiments, the cutting mechanism (104) may be dome-shaped. In some embodiments, the cutting mechanism (104) may be activated upon receiving a signal (e.g., an electrical stimulus, etc.), whereupon receiving the signal, the cutting mechanism (104) deploys, assuming a desired (e.g., pre-configured) conformation (e.g., deploys from the needle). In some embodiments, the deployable cutting mechanism (104) may be operatively connected to an electrocautery system that can activate the deployable cutting mechanism (104) (when desired) for cauterization.

The biopsy system (100) of the present invention is adapted to be rotated and to cut/cauterize tissue, harvesting the tissue in a spiral or corkscrew configuration. Suction may be applied to help withdraw tissue. Non-limiting examples of mechanisms for generating a suction or vacuum include a DC motor vacuum pump, a syringe created vacuum, or an external pump and tether. The distal end of the needle is inserted into the tissue needing a biopsy sample. The sheath (103) is withdrawn and the cutting mechanism (104) (e.g., a cauterizing wire in one embodiment) is exposed (e.g., springs out, extends out, is pushed or forced out, etc.) from the aperture (102). Suction is applied. With suction and cauterization underway, the needle (101) is retracted or advanced while being rotated, resulting in a spiral column or coil of tissue entering into the aperture (102) and lumen (106) of the needle.

Figure 26B:
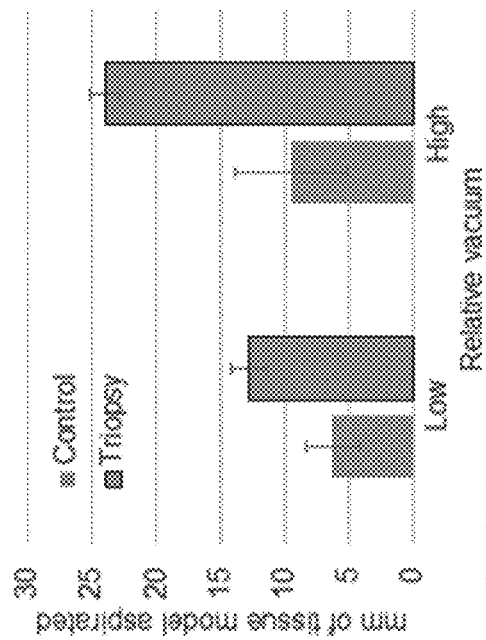
FIGS. 26A-26C show a 3D printed cutting dome-type prototype needle, referred to herein as "Triopsy" needle, and results thereof when compared to an exact-sized standard full-core needle.
Figure 26C:
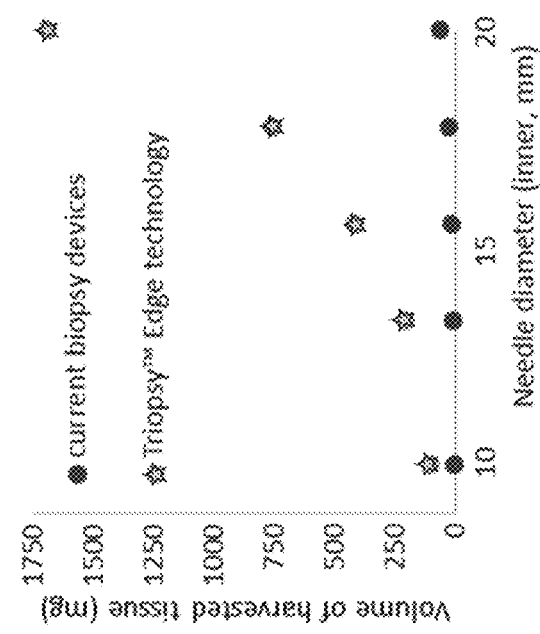

Without wishing to limit the invention to a particular theory or mechanism, the system (100) can allow for harvesting larger amounts of tissue as compared to core biopsy needles. In some preferred embodiments, the volume of tissue may be calculated using the following equation: $V=\pi r^2 * 2\pi R * n$, wherein r=radius of tissue, R=radius of coil (or expandable wire sweep radius), and n=number of coils or turns. In contrast, current biopsy devices can at maximum harvest volumes according to the equation $V=\pi r^2 * h$. FIG. 26C shows theoretical volumes of harvested tissue (mg) using various sizes of needles, comparing current biopsy devices with the system of the present invention. The system of the present invention allows for increased tissue harvesting, and the number of coils can help increase the volume of tissue that is harvested. Further still, it is believed that the ability to harvest larger volumes of tissue in a single pass may potentially reduce biopsy-associated complications, e.g., complications associated with multiple passes through tissue, and reduce procedural time.

Again, without wishing to limit the present invention to any theory or mechanism, it is believed that the present invention is advantageous as more tissue can be harvested in a single pass, and more tissue may help provide more confident primary diagnoses, specialized testing for tailored therapy, and may allow for portions of specimen to be allocated toward research purposes for improved understanding of basic biology. Additionally, by having fewer passes through the tissue (and thus less bleeding risk but better yield), there may be less hesitation to order biopsies, and the increased frequency of tissue sampling may improve monitoring of treatment response so that patients aren't uselessly exposed to (possibly dangerous) therapies while enhancing our understanding of clinical biology. Lastly, the capabilities of the device may be enough to remove certain (small) lesions, resulting in both a diagnostic and therapeutic minimally-invasive procedure, especially in resource-limited areas where excisional biopsies with safe anesthesia and surgical facilities are limited.

As previously discussed, the present invention may feature more than one lumen (106). In some embodiments, the system comprises a lumen (106) for holding a solution (e.g., saline, medication, etc.). As a non-limiting example, in some embodiments, the solution may comprise a pro-coagulant slurry that may be used in combination with or in lieu of cauterization. In some embodiments, a lumen (106) is disposed in the needle and is fluidly connected to another part of the system, e.g., the aperture (102) and/or deployable cutting mechanism (104) and/or distal end of the needle, etc. In some embodiments, a lumen (106) is disposed outside of the needle but is fluidly connected to another part of the system, e.g., the aperture (102) and/or deployable cutting mechanism (104) and/or distal end of the needle, etc. The system (100) may further comprise mechanisms for moving the solution in the lumen to an area of interest. For example, a solution from the lumen may be injected into the biopsy site or other appropriate location (e.g. needle tract). In other embodiments, the lumen (106) can also be used for the insertion or withdrawal of a guide wire and/or the insertion of a radio-opaque marker.

In some embodiments, ultrasonic vibrations or other appropriate mechanisms may be used to help determine a location of the system within the tissue or help guide the system in the tissue. For example, the system may be activated in a way (e.g., buzzing) so that it can be better visualized using ultrasound. In other embodiments, the system may transmit a different type of signal that can allow for better visualization and/or positioning.

The system of the present invention may be used in combination with cauterization. In some embodiments, the system comprises a component that helps reduce the amount of harvested tissue that is burned from cauterization. For example, the system may insulate the cauterization/coagulative surface from the cutting edge. In some embodiments, the deployable cutting mechanism (104) is shaped such that it has two sides, a first side and a second side. In other embodiments, the deployable cutting mechanism (104) may comprise a first side that is a cutting edge and a second side that has a cutting coagulating edge. The coagulating edge may be a portion of the second side, e.g., the coagulating edge may be designed to only contact tissue that is the patient's remaining tissue and not the harvested tissue.

In some embodiments, insulation of the harvested tissue from cauterization/coagulation may be achieved using vibration and a micro-serrated edge to cut. For example, a back-and-forth sawing motion cuts the tissue. The cauterization surface (161) on the top of the deployable cutting mechanism (104) cauterizes the top portion of the tissue, while the bottom portion of the issue is insulated. The cauterization surface (161) may be derived from a conducting wire extending through the deployable cutting mechanism. In some embodiments, the deployable cutting mechanism (104) comprises an insulating component (162) (e.g., insulating encasement). The cauterized or singed surface in the patient heals, and the clean-cut sample is suctioned or directed through the lumen in the needle.

In some embodiments, the system of the present invention is used with pulsed electrical currents that have been shown to burn only about a single cell-layer deep (see Plast Reconstr Surg. 2009 December; 124(6):1849-59. Comparative healing of surgical incisions created by the PEAK PlasmaBlade, conventional electrosurgery, and a scalpel. Loh S A, Carlson G A, Chang E I, Huang E, Palanker D, Gurtner G C.). For example, the system may incorporate a device such as a Pulsed Electron Avalanche Knife (PEAK) PlasmaBlade or similar technology, which uses high frequency electrical pulses, to help cut without burning the tissue.

According to some other embodiments, the present invention also features methods for obtaining biopsies. The method may comprise inserting the system into the tissue of concern, exposing the (deployable) cutting mechanism, creating suction, and optionally preparing the needle for rotation (e.g., winding a spring to spin the rod). In one embodiment, these steps may be simultaneously performed in a single step, e.g., using a single motion or activation. In some embodiments, the method may further comprise activating cauterization, spinning the rod, and opening the suction/vacuum to start harvesting of the tissue. These steps may be simultaneously performed in a single step, e.g., using a single motion or activation. In some embodiments, the system can be loaded with two hands, or in some instances, just one hand is needed to activate the system. Alternatively, in some embodiments, the system utilizes a vacuum creation/winding motion to load, and the system utilizes a safety-type thumb trigger to deploy the needle, and finally the trigger to engage, which may only require one hand, and the other hand can be on an ultrasound probe. In some embodiments, the method is performed by the operator in three or four actions. In some embodiments, the method is performed by the operator in three or less actions. In other embodiments, the method is performed by the operator in more than four actions.

In some embodiments, the geometry and function of the deployable cutting mechanism may involve a filament with an insulating surface and a conductive surface ranging from 1 µm to 5 µm apart such that the tissue being cut would be spatially separated from the conductive surface delivering electrocauterization or electrosurgical current.

Additional features of the system include multi-lumen needle geometry and diameter, needle material, deployable cutting mechanism configuration, the deployable cutting mechanism material, the electrical current amplitude and frequency and potential inductance when coupled to a deployable cutting mechanism of the needle, the resulting thermal/electrical injury or necrosis of the tissue sample after exposure to electrical current, the negative pressure of suction to aspirate tissue without inducing acute pressure-necrosis, the geometry of the deployable cutting mechanism and frequency of vibration/sound to enhance ultrasound localization, etc.

The present invention is not limited to the aforementioned configurations. For example, in some embodiments, the system features a needle that cauterizes as it leaves the biopsied tissue to help decrease bleeding. In some embodiments, the system features a deployable cauterization ring. In some embodiments, the system features a tip of the needle that pops out or off, after which the needle can be spun and tissue may be suctioned. In some preferred embodiments, the tip of the needle that pops out or off remains in the tissue as a biopsy tissue marker. Tissue biopsy markers or small metal clips may be placed within the tissue at the time of biopsy to help identify the location of the target tissue, e.g. lesion, in the future. Without wishing to limit the invention to a particular theory or mechanism, by having a needle tip that is removable, this may decrease procedural time and overall expenses.

In other embodiments, the system of the present invention may be constructed from a variety of materials. For example, in some embodiments, the needle and/or deployable cutting mechanism may be constructed from a material comprising metal and/or plastic and/or a ceramic material. The present invention is not limited to these materials.

Further details of the biopsy needle system of the present are presented in the following sections. It is to be understood that the system is not limited to the configurations that will be described herein. Equivalents or substitutes are within the scope of the invention.

Figure 1B:
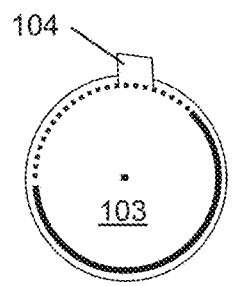
Figure 1C:
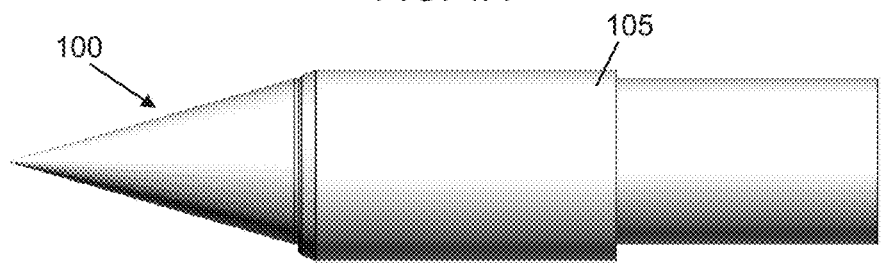
Figure 1D:
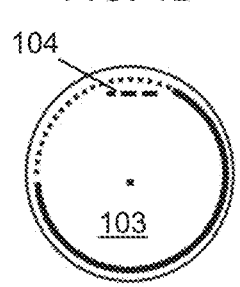

Referring now to FIG. 1A, a hollow needle (101) of the biopsy needle system may have an aperture (102) near the distal end, a sharp conical tip (103) affixed to a cutting element (104), and a retractable movable sheath (105). Retraction of the sheath (105) exposes the hollow needle (101), aperture (102), and allows for expansion of the cutting element (104). FIG. 1B demonstrates the hollow needle with aperture and cutting element within the sheath, with the tip exposed. The cutting element (104) is collapsed near the distal end. Dashed lines represent objects obscured from view.

Figure 2A:
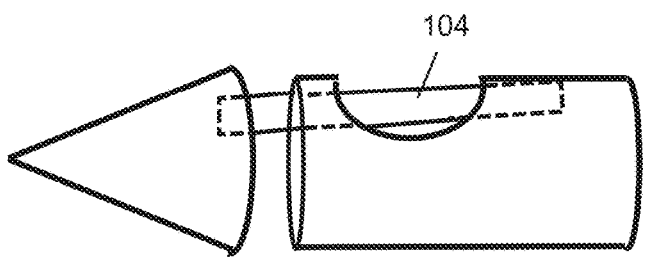
FIGS. 2A-2C show another non-limiting embodiment of the biopsy needle device. Dashed lines represent objects hidden from view.
Figure 2B:
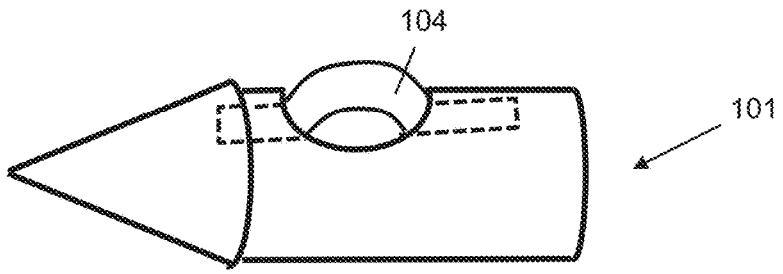
Figure 2C:
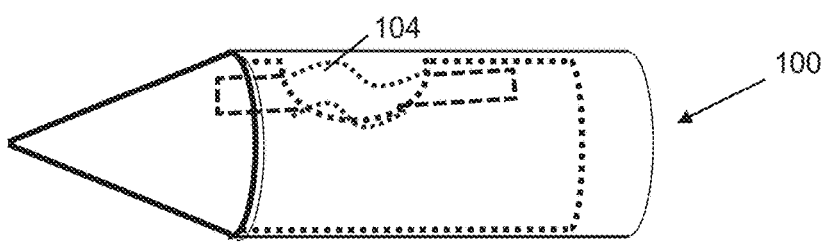

FIG. 2A shows the hollow needle (101) with an aperture (102) near the distal end, a sharp conical tip (103) affixed to the cutting element (104), which may be a sharp filament or ribbon, and the cutting element then joined to the hollow needle proximal to the aperture. FIG. 2B shows the conical tip (103) affixed to the cutting element and hollow needle, with resultant outward bowing of the sharp cutting element through the aperture. Dashed lines represent portions obscured from view.

As shown in FIGS. 4A, 4B, and 5, in some embodiments, the biopsy needle system may comprise a deployable flexible cutting paddle (104) with attachable sharp tip (103). The paddle may be placed in the distal end of the needle and the cone tip (103) inserted on the end of the hollow needle, thereby holding the cutting element (104) in place. As shown in FIGS. 6A-6G, in other embodiments, a raised cutting sharp-edged, semi-dome (104) over the aperture could be used instead of a filament. FIGS. 6F-6G are of a flexible overlying sheath (105) that would protect tissue from being cut by the sharp dome until the sheath (105) is retracted.

Referring to FIGS. 7A-7E, varying configurations of the system (e.g., rods) may include a main lumen (106) for tissue, a cutting portion (deployable cutting mechanism) (104), a lumen (106) for said cutting portion, and a localizing wire hole (107), which may be a portion of wire or needle wall. Referring to FIG. 8, multiple lumen geometries may include a main lumen (106a) for suctioning tissue, which is shown as the largest circle or oval, a second lumen (106b) for the cutting element or as an injection port, and optionally, a third lumen (106c) specifically for the cutting element. In some embodiments, the second lumen (106b) may be adjacent to or overlapping the third lumen (106c). In other embodiments, the third lumen (106c) may be overlapping the second lumen (106b). Referring to FIGS. 9A-9C, in some embodiments, the sheath (105) may be circular cylindrical, or alternatively, may have an oblong, oval, or teardrop cross-sectional area, allowing for the expanded cutting surface to be affixed on the outside of the needle, or even within a second lumen as part of the hollow needle.

Figure 10:
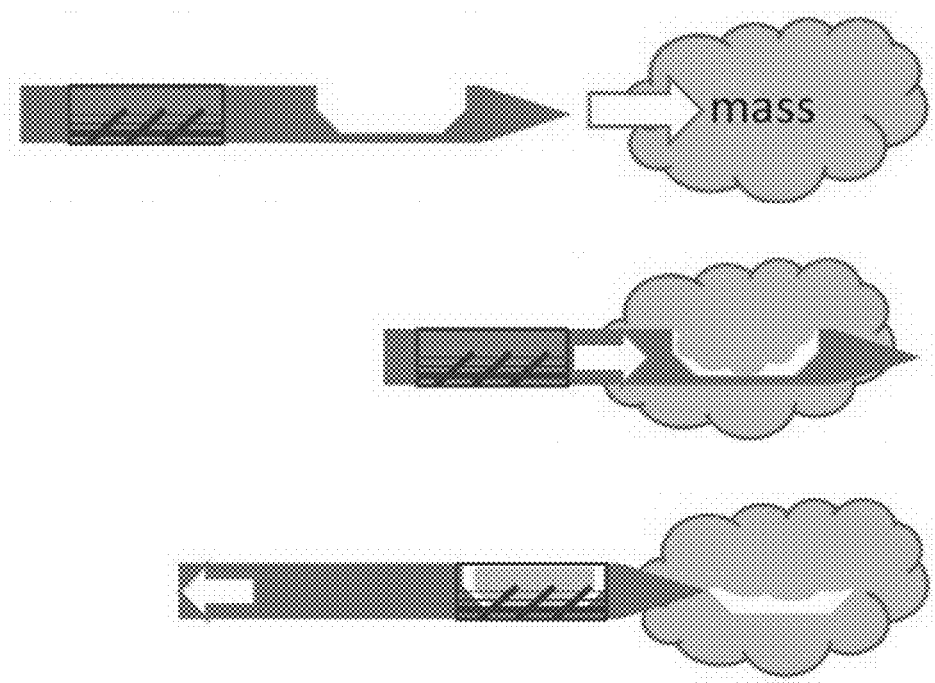
FIG. 10 demonstrates a prior art needle biopsy procedure using side-notch technology.
Figure 11:
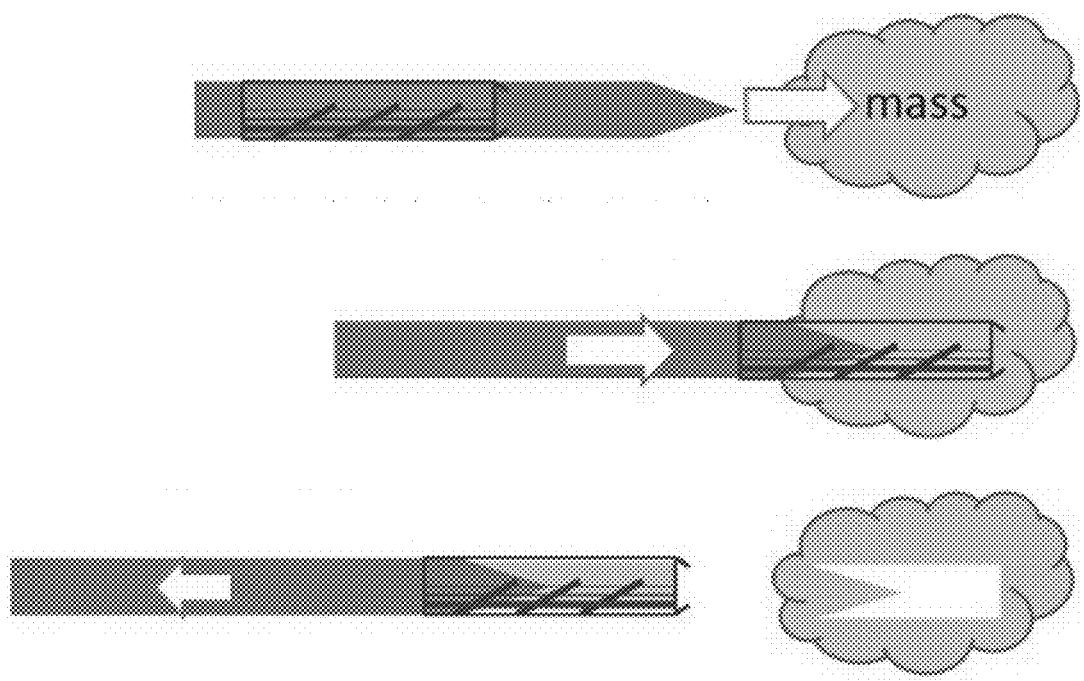
FIG. 11 shows another prior art needle biopsy procedure using full core technology.
Figure 12:
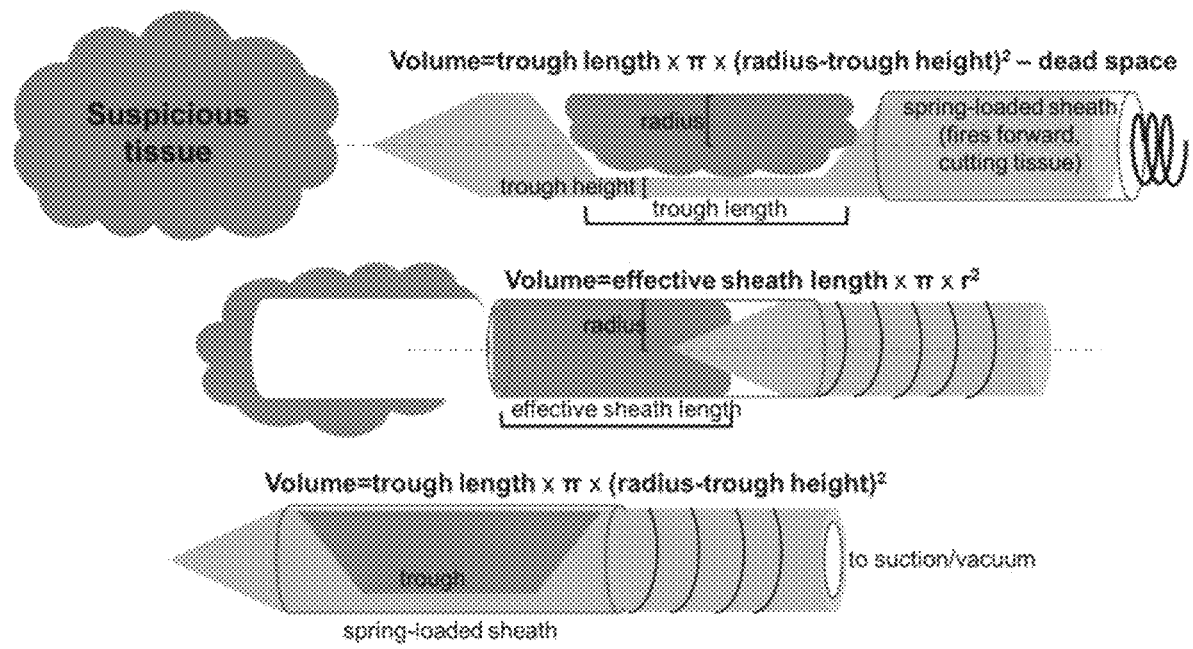
FIG. 12 shows another view of the prior art procedures of FIGS. 10 and 11.

FIGS. 10-12 are provided for comparison with current biopsy procedures known in the art. In FIG. 10, a partially hollow needle is placed in the mass under question. After the mass is allowed to expand into the hollow area, a sheath fires and cuts a core. The sheath and needle are then withdrawn and the core is removed. Referring to FIG. 11, a needle (bearing a sheath with teeth on the far end) is inserted into the mass under question. The sheath is fired into the mass and then the needle, sheath, and full core of tissue is removed. As shown in FIG. 12, in a vacuum-assisted biopsy procedure, similar to the side-notch procedure except with a hollow needle and vacuum, a notched needle is placed in the tissue under question. Thereafter, suction is applied and more tissue forced into the trough, before firing of the sheath cuts the suctioned tissue, which is then transmitted towards the vacuum source. The resultant volume of tissue comprises harvested tissue per needle pass. In a full-core type, the biopsy needle with a sheath fires forward and cuts a core of tissue and the volume thereof. A vacuum is used to assist in trough/side-notch biopsy needle systems and the volume of tissue harvested per pass of the sheath.

Figure 13:
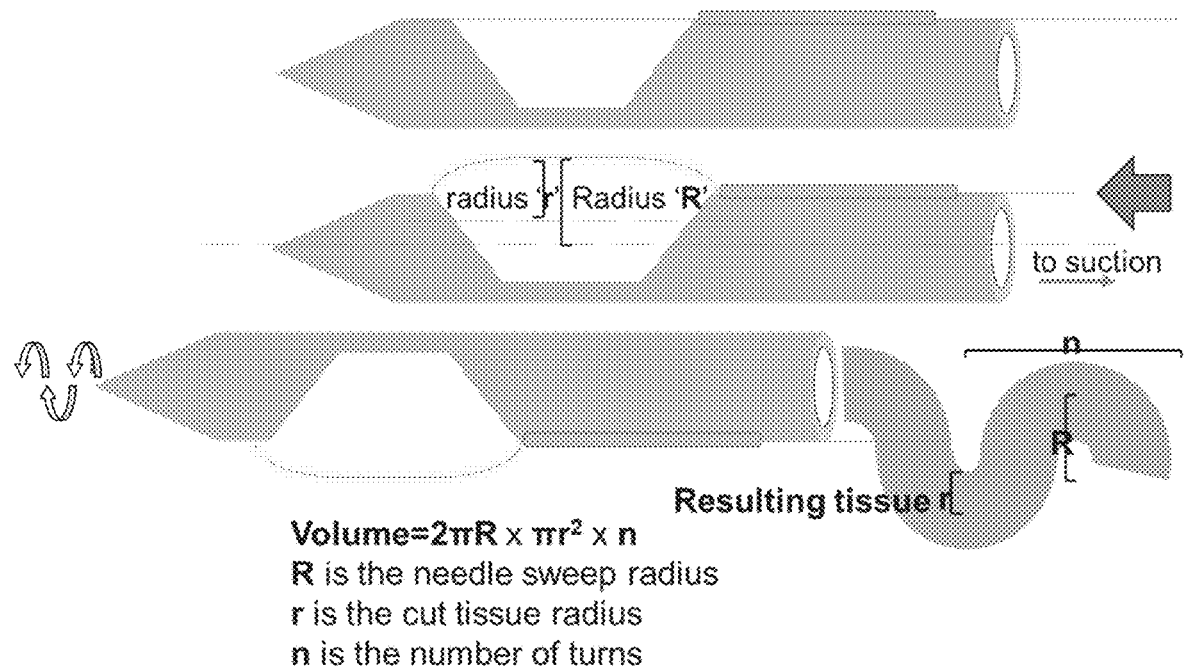
FIG. 13 illustrates an exemplary mechanism utilizing the biopsy needle system of the invention.

Referring to FIG. 13, the present invention employs a biopsy procedure where the distal end of the needle (101) (with or without a sheath covering the opening/aperture) is inserted into the tissue under question. A cutting/cauterizing wire (104) is deployed from the aperture via a push-mechanism in this iteration. Suction is applied to the back end of the needle. The needle is advanced while being rotated, resulting in a spiral column or coil of tissue entering into the aperture (102) and lumen (106) of the needle, resulting in a coil of tissue.

Figure 14A:
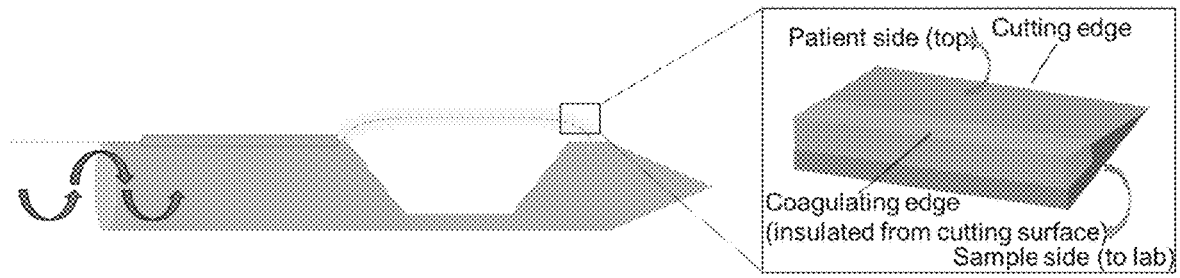
FIGS. 14A-14C show alternative embodiments of the biopsy needle device having a deployable cutting element having a cutting edge and a cauterizing edge for coagulation, as well as an insulator and an expandable foil or mesh scoop.
Figure 14B:
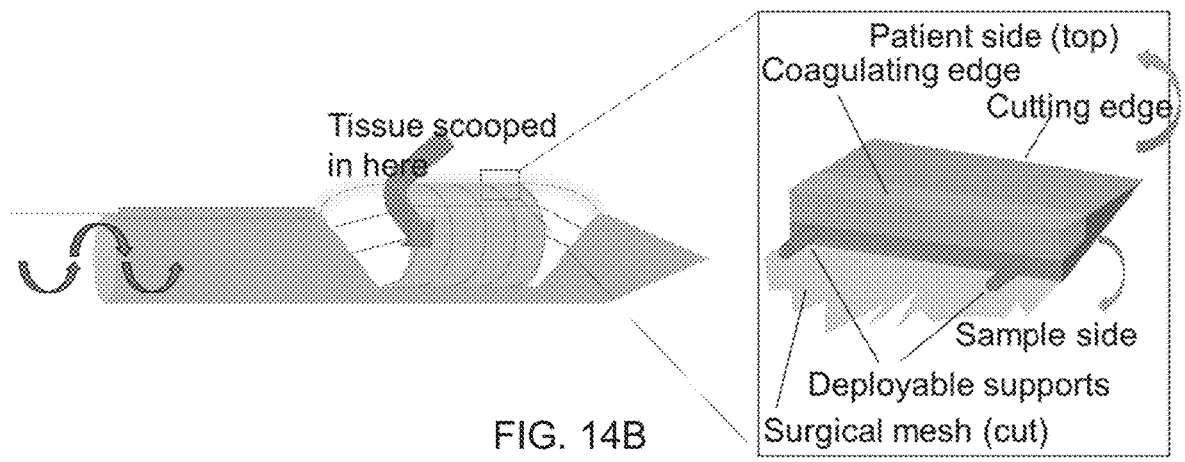
Figure 14C:
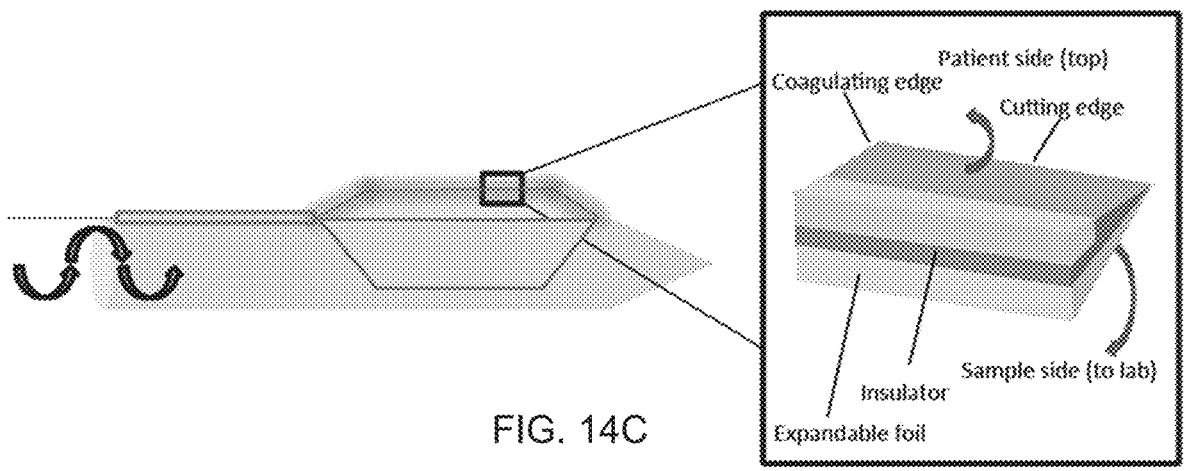
Figure 15:
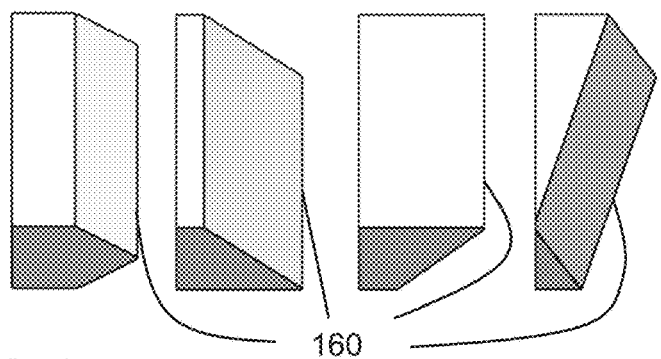
FIG. 15 shows multiple embodiments of cutting element geometries, such as a double-sided wedge, single-sided wedges at different orientations, or a diagonal single-sided wedge.

FIG. 14A shows a detailed view of a deployable cutting mechanism (104) comprising a cutting edge (160) and a coagulating edge (161). FIG. 14B shows a detailed view of a deployable cutting mechanism featuring a cutting edge and a coagulating edge, as well as deployable flexible supports and expandable surgical mesh to direct tissue into the aperture/lumen. FIG. 14C shows a deployable cutting mechanism featuring a cutting edge and a coagulating edge, as well as an insulator and an expandable foil scoop to direct tissue into the aperture/lumen.

Figure 16A:
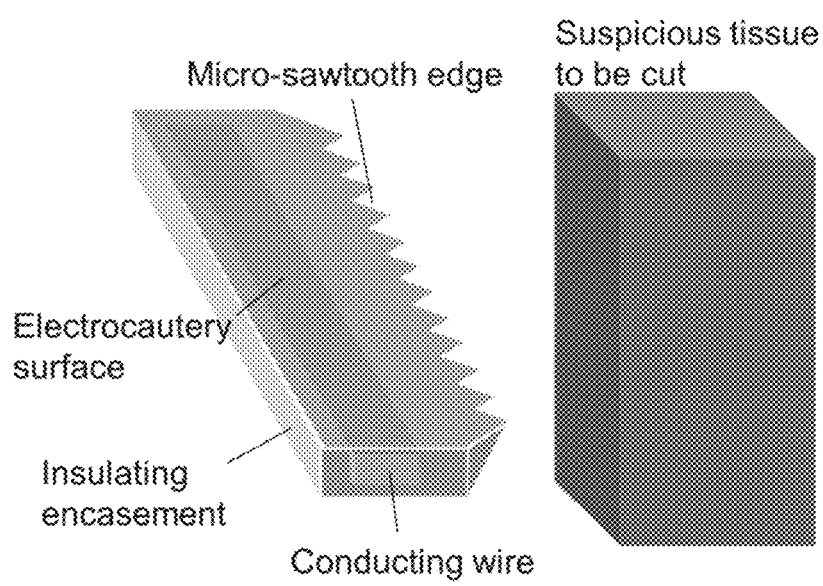
FIGS. 16A-16B show a deployable cutting mechanism with a micro-serrated edge for cutting and a cauterizing surface for coagulation.
Figure 16B:
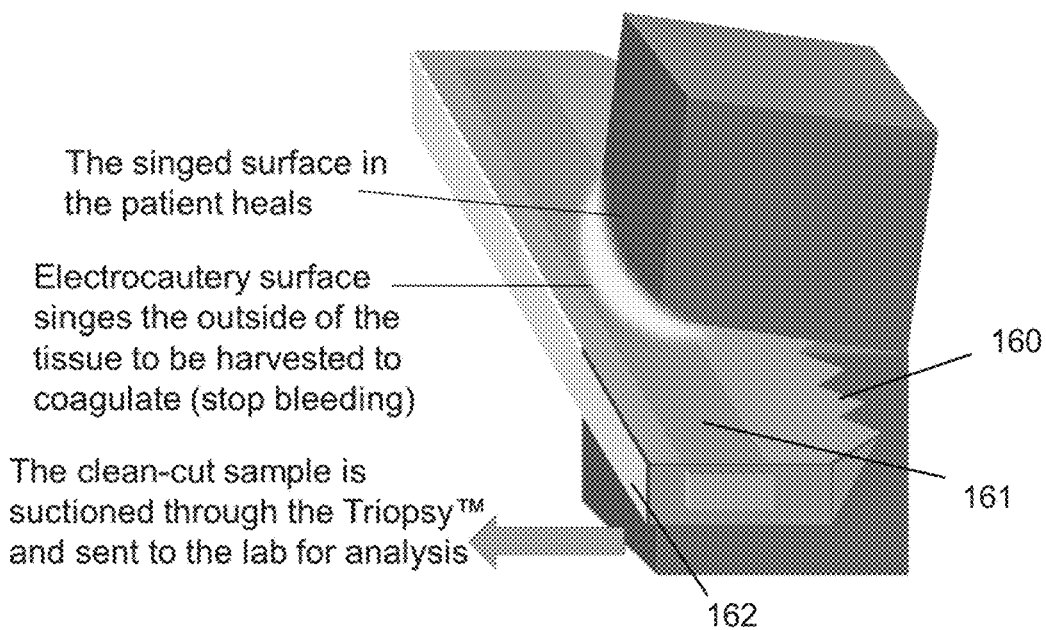

As shown in FIG. 16A, in some embodiments, the cutting mechanism may feature a micro-serrated edge for cutting the tissue via a back-and-forth sawing motion. As shown in FIG. 16B, the cauterization surface on the top of the deployable cutting mechanism can cauterize the top portion of the tissue, while the bottom portion of the tissue destined for the aperture, lumen, and eventually the lab, is insulated.

Figure 17A:
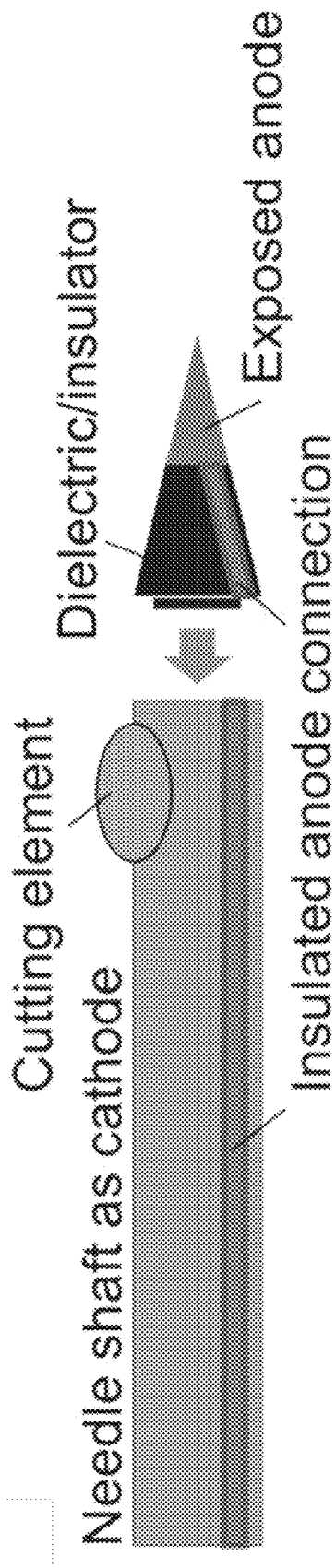
FIGS. 17A-17B show alternative electrocautery/electrosurgical configurations of the device.
Figure 17B:
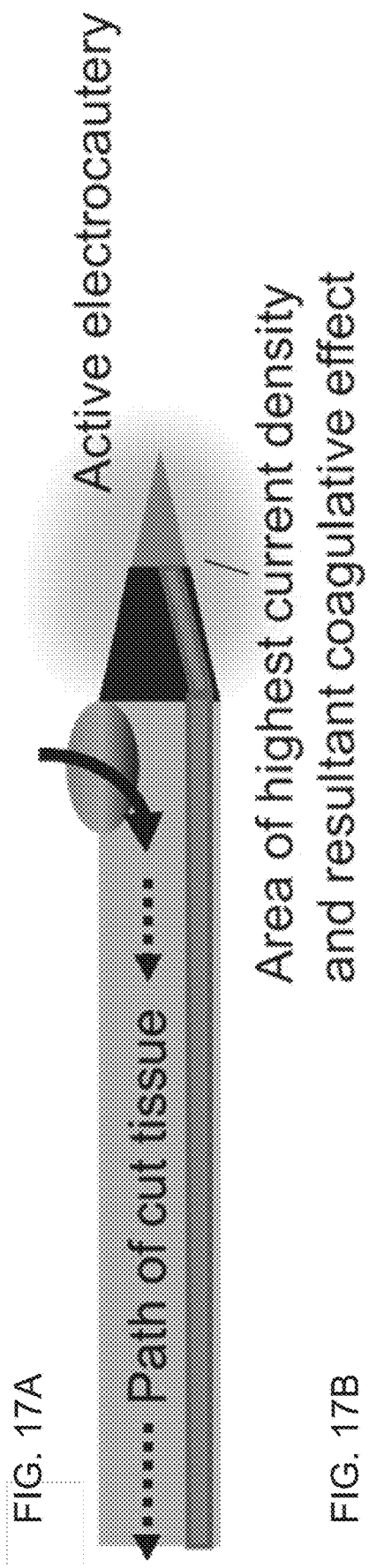

Referring to FIG. 17A, the needle shaft acts as a cathode and an insulated anode runs along the needle shaft or alternatively, through a second lumen before connecting to a dielectric/insulator and exposed anode on the distal needle tip. Referring to FIG. 17B, active electron flow results in maximal coagulative effect over the distal needle tip, sparing the cut tissue sample from any electrical or thermal damage.

Figure 18A:
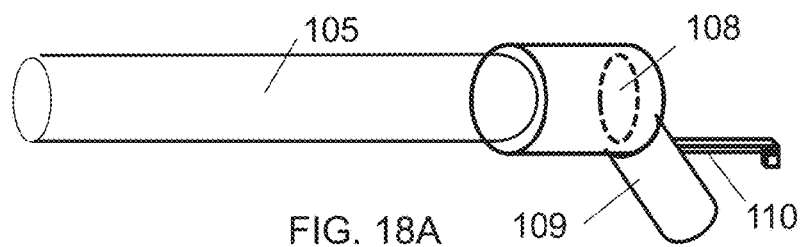
FIGS. 18A-18C show a non-limiting embodiment of a sheath component of a biopsy needle system having a port at the back end to accept the biopsy needle, a side port for injections or placement of a guide wire, and a connection to a retraction mechanism.
Figure 18B:
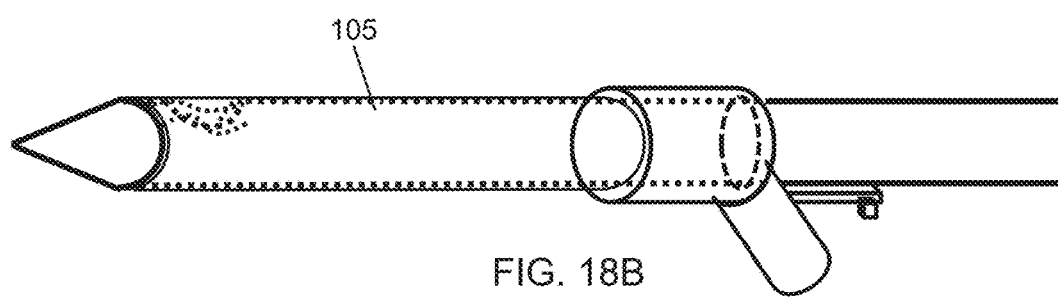
Figure 18C:
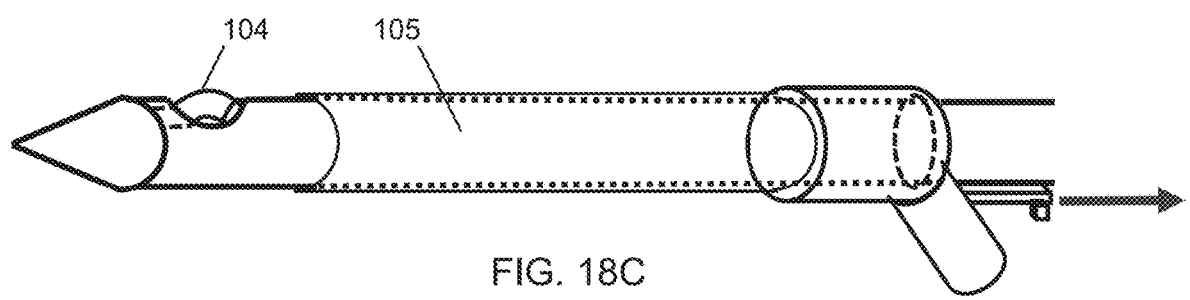
Figure 19A:
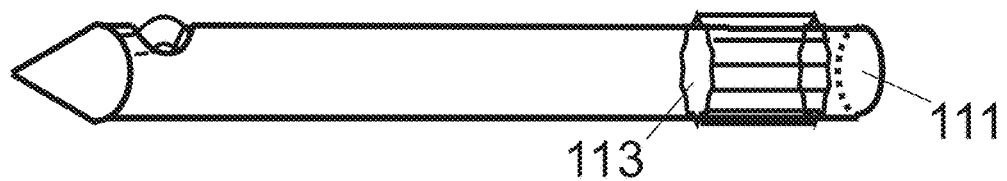
FIGS. 19A-19B show an embodiment of the biopsy needle system having a gear to transmit rotational force.
Figure 19B:
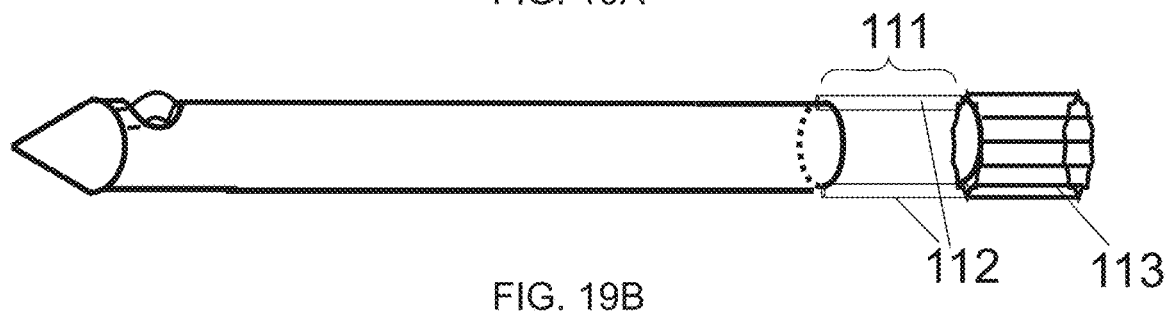

FIG. 18B shows the sheath with the biopsy needle and resultant coverage of the cutting edge by placement therein. As shown in FIG. 18C, a backward force on the posterior connection (110) causes retraction of the sheath (105), resulting in exposure of the cutting edge (160). In one embodiment, FIG. 19A shows the back end of the needle containing an opening for tissue to be suctioned into a vacuum collection chamber (115), and connections (112) to the needle body to transmit rotational force, such as from a gear (113). In some embodiments, the collection chamber (115) may have a transparent window or the chamber itself may be substantially transparent in order to view the amount of tissue collected and the presence/absence of blood, etc. Dashed lines represent objects or surfaces hidden from view. In another embodiment, FIG. 19B shows a different possible configuration with the mode of rotational force transfer as in a hollow gear (113) could be on the front of the posterior needle opening (111) for tissue to be suctioned into the collection chamber.

Figure 20A:
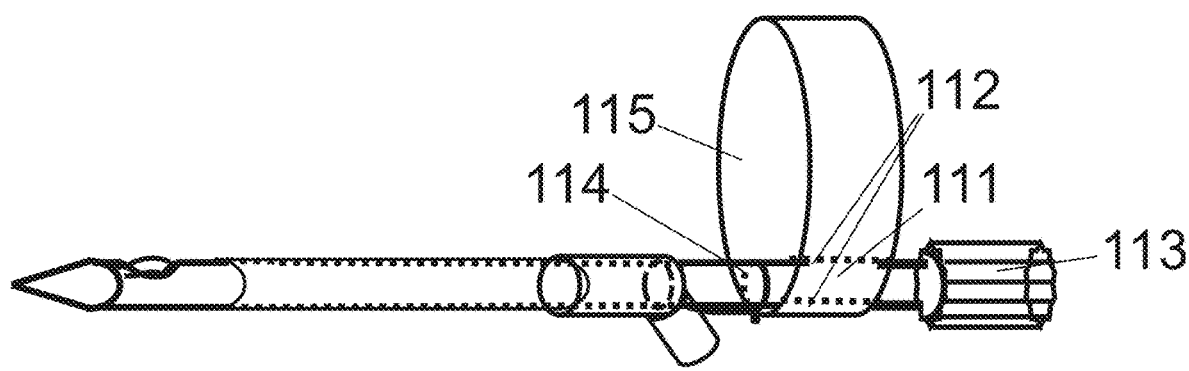
FIGS. 20A-20G show an embodiment of the biopsy needle system having a vacuum collection chamber coupled to a vacuum source and a needle rotating mechanism.
Figure 20B:
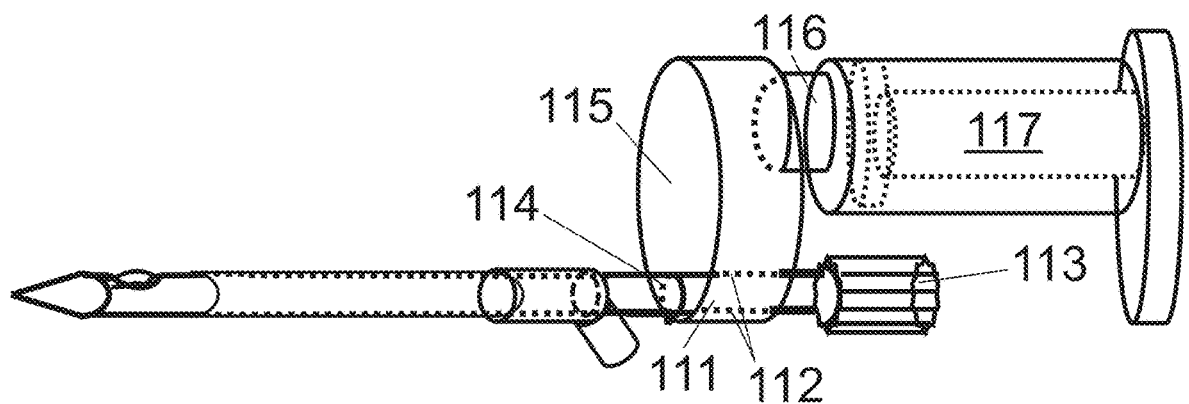

In one embodiment, FIG. 20A shows the collection chamber (115) for storing the suctioned tissue. An air-tight seal (114) about the proximal needle affixes the vacuum collection chamber (115) to the needle. In this example, the vacuum chamber is cylindrical. In one embodiment, FIG. 20B demonstrates one way to generate negative pressure in the tissue collection chamber. An attachment (116) from the vacuum collection chamber (115) to a syringe (117) enables negative pressure at the back end of the needle. Alternatively, the syringe may be replaced with an external vacuum source via an appropriate attachment.

Figure 20C:
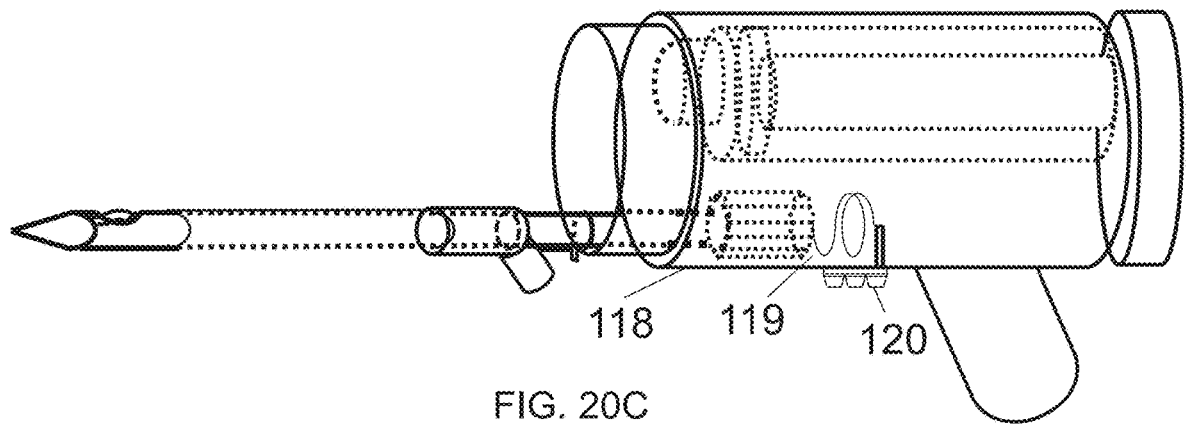
Figure 20D:
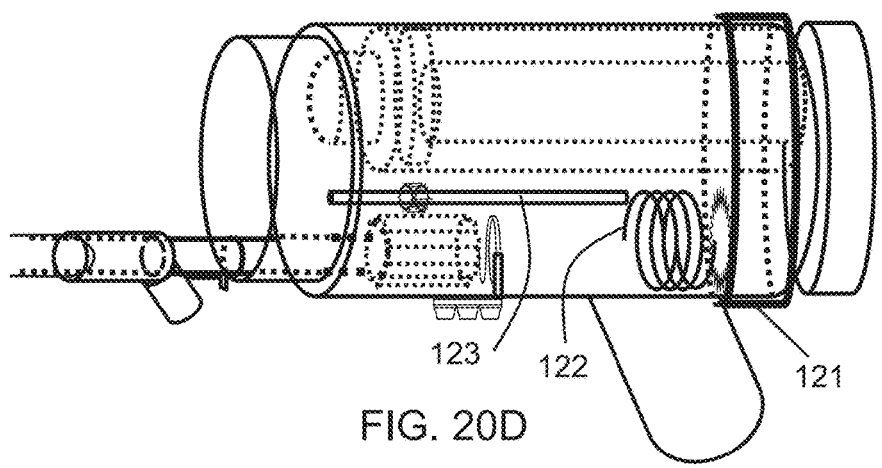
Figure 20E:
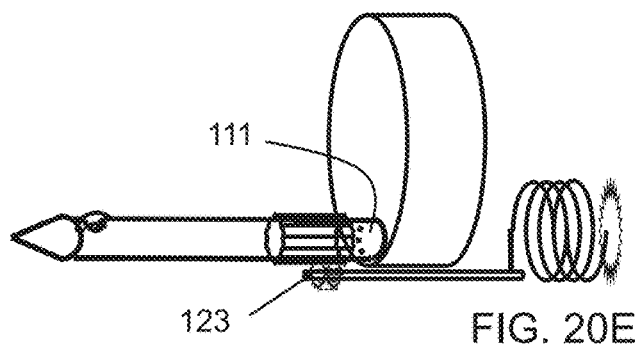
Figure 20F:
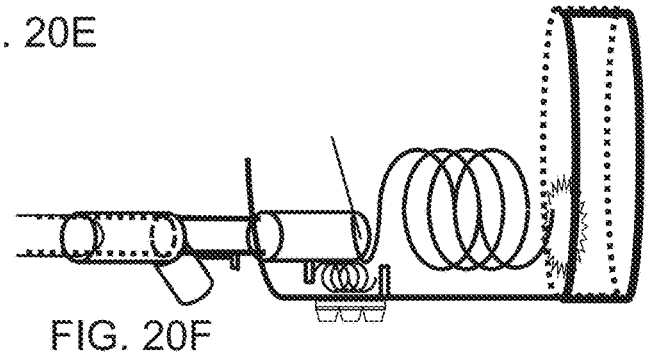

FIG. 20C is a non-limiting embodiment of an encasement (118) adjacent to the vacuum collection chamber (115) housing the attached syringe/vacuum source, and needle rotating mechanism. As forward-throwing spring-loaded biopsy devices can present a danger to patients, a means of drawing back the needle as it rotates, in this case a small spring (119), is within the encasement. A means for the user to adjusting how far the needle withdraws as it rotates and the resultant gross length of harvested tissue, such as a switch (120) attached to the spring, is present. A handle to the encasement may be added. Alternatively, the biopsy system encasement and controls may be sufficiently ergonomic such that a handle is not required In some embodiments, FIG. 20D shows a means for the user to adjust the rotational force, in this case, a dial (121) attached to a second larger spring (122), and thus axially rotate the needle. The dial (121) on the exterior of the encasement can adjust the tension on the large spring (122) within the encasement in this embodiment. In other embodiments, a means of transmitting the rotational force to the needle is needed. For example, said means may be a rod with gear (123) in contact with the gear on the back of the needle. FIG. 20E shows the rod and gear (123) as a means of transmitting rotational force to the needle when the needle body gear is in front of the posterior opening (111) of the needle. In yet other embodiments, as shown in FIG. 20F, an alternative means to adjust and apply the rotational force (e.g. dial and spring) may be configured in relation to the posterior end of the needle to bypass the need for any encased intermediary mechanism (e.g. rod and gears). One skilled in the art may affix an electric motor that provides for rotational and retractional force upon the needle instead of the spring mechanism.

Figure 20G:
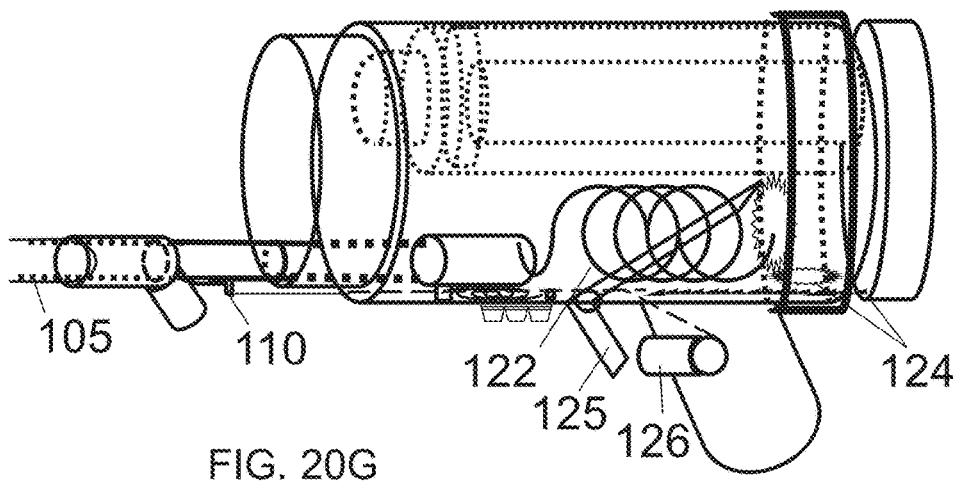

In some embodiments, as shown in FIG. 20G, a toothed rod and gear (124) representing one embodiment of a means of generating rotational energy transmitted to the needle via a large spring (122). A trigger (125) is in connection with the large spring as a way to control the release of energy and eventual rotation of the needle. In other embodiments, a safety switch (126) is included for disabling pulling of the trigger and is in connection to the posterior element (110) of the sheath (105) covering the needle. In other embodiments, the trigger (125) may be an "on-off" switch for an electric motor in embodiments where a motor, instead of a spring, provides rotational forces.

Figure 21A:
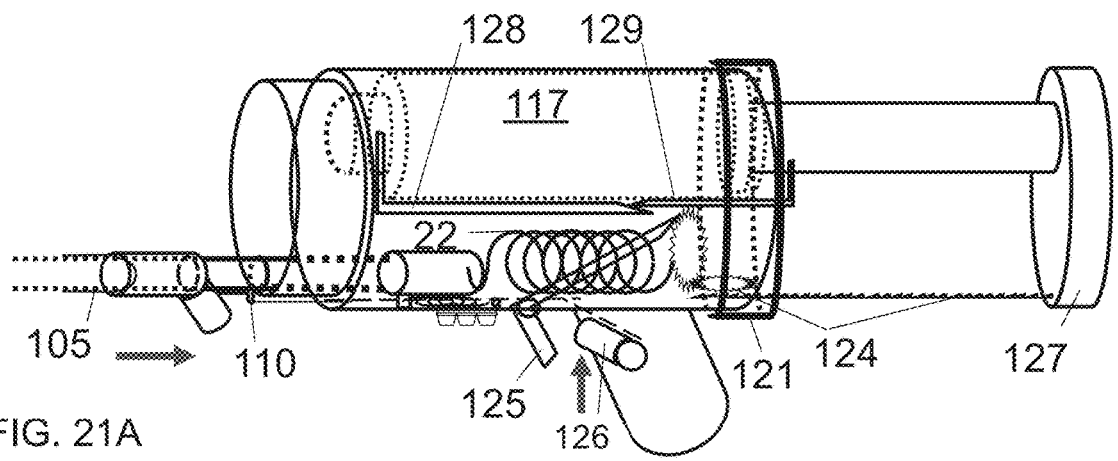
FIGS. 21A-21D illustrate configurations of the biopsy needle system during use, namely, rotation of and suction within the needle results in cutting of tissue and suction of the cut tissue into the collection chamber.

FIG. 21A shows how pulling of a plunger (127) winds the large spring (122) via the toothed rod and gear (124), creates negative pressure in the syringe (117), and posteriorly displaces the dial (121) for adjusting the eventual number of needle rotations. In some embodiments, a one-way valve (128) and/or a syringe lock (129) can maintain the negative pressure created by the syringe. In other embodiments, lifting of the safety switch (126) can pull the posterior element (110) of the sheath (105) and expose the cutting element.

Figure 21B:
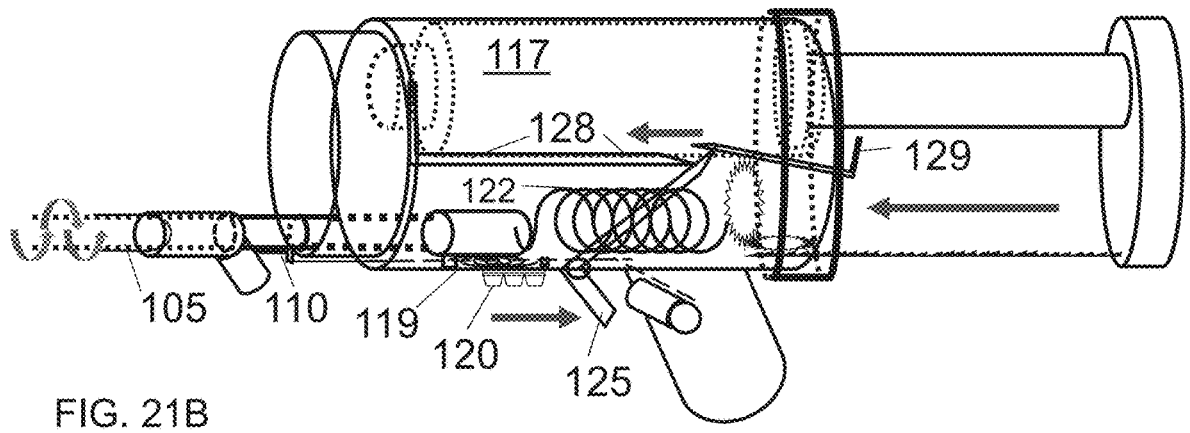
Figure 21C:
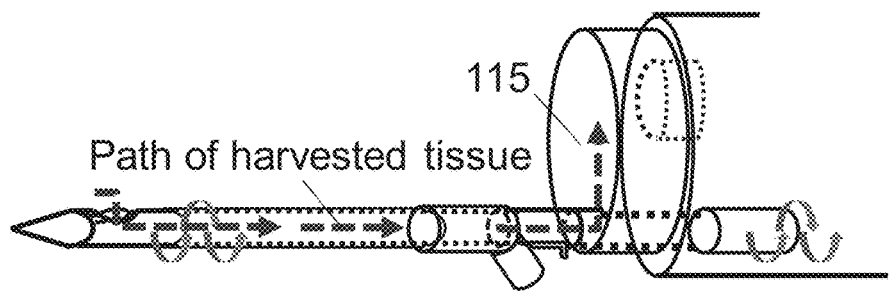
Figure 21D:
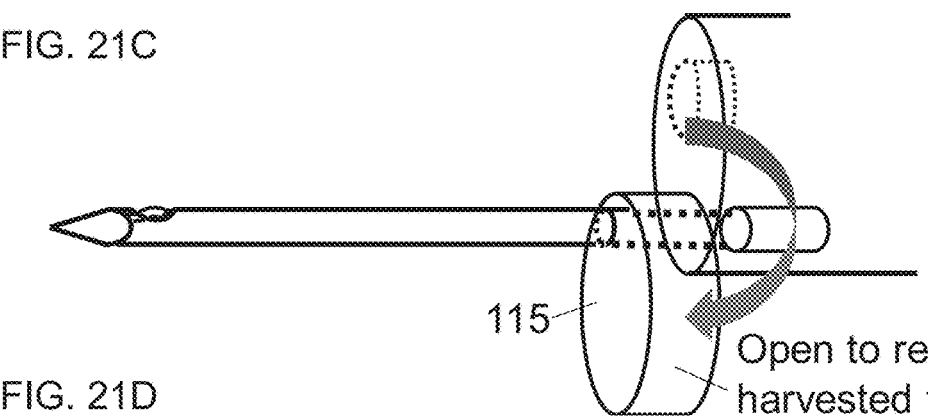

Referring to FIG. 21B, in some embodiments, pulling the trigger (125) may release the vacuum valve (128), syringe lock (129), and wound-up spring (122), thereby causing both suction within the needle and rotation of the needle in relation to the sheath (105). The smaller spring (119) can pull on the back of the needle per the user's adjusted switch (120), thereby retracting the exposed cutting spinning needle element. FIG. 21C is of the needle and sheath portion of the system. Rotation of and suction within the needle results in cutting of tissue and suction of the cut tissue into the collection chamber (115). In some embodiments, similar to FIG. 18A, the needle portion can be removed, optionally leaving the sheath in place after harvesting of adequate tissue. In other embodiments, as shown in FIG. 21D, the sheath (105) can be removed, the collection chamber (115) can be opened, and the harvested tissue retrieved.

Figure 22A:
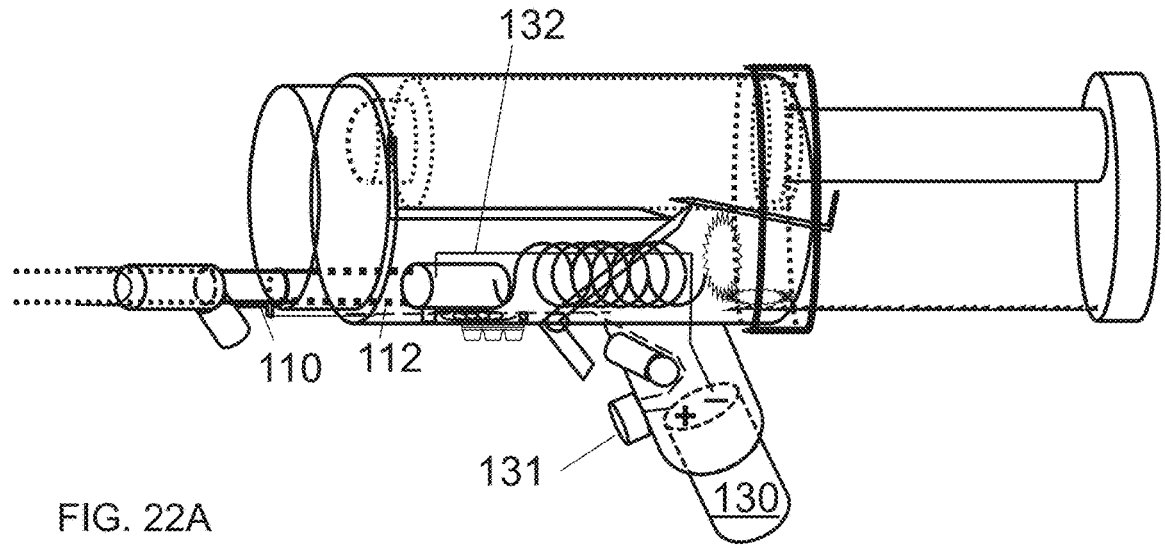
FIGS. 22A-22C show a non-limiting embodiment of the biopsy needle system capable of electrocoagulation during the biopsy procedure.
Figure 22B:
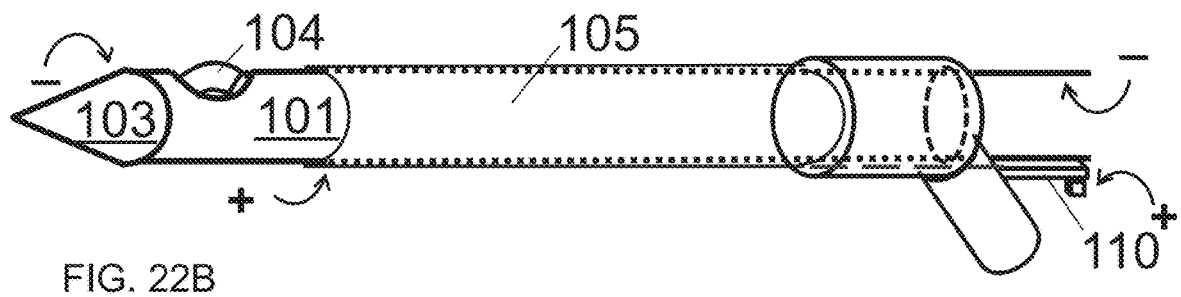
Figure 22C:
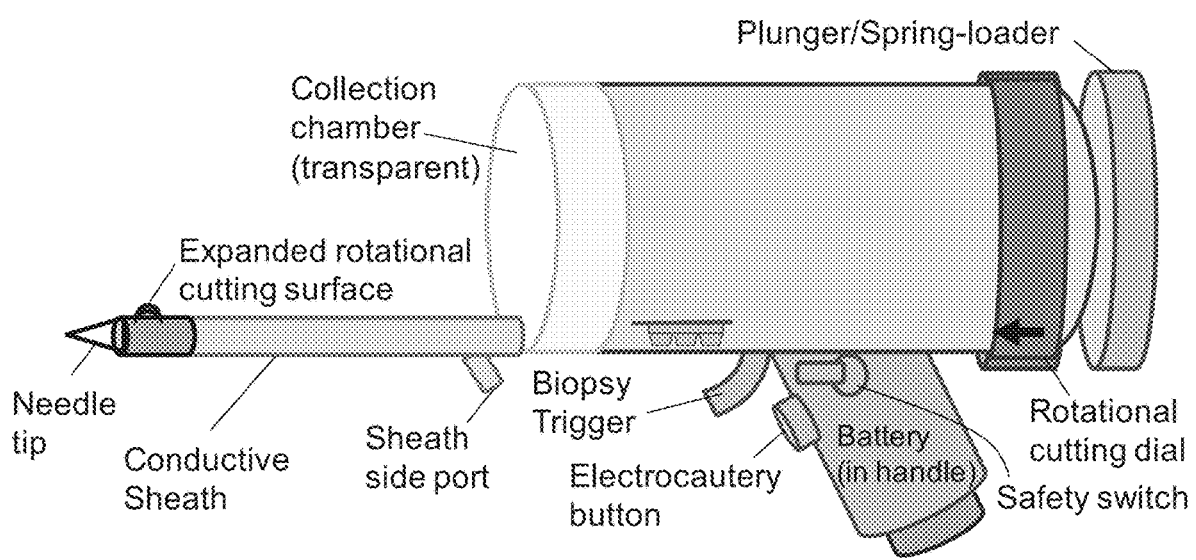

While the sheath provides for a method to inject clotting material, in other embodiments, electrocautery or electrosurgery may be employed to cause electrocoagulation during the biopsy procedure as a different means of stopping bleeding. In one embodiment, FIG. 22A shows an electrical source, in this case a battery (130), in connection with a button (131) completing a circuit via an electrical connection (132) to the inside of the needle. In one embodiment, the exterior of the needle may be insulated. Alternatively, the expanded cutting element (104) may run the length of the needle, as shown in FIG. 4A. Referring to FIG. 22B, the needle or expanded cutting element (104) may be in contact with the conductive needle tip (103), completing one aspect of the circuit from inside the needle. The second portion of the electrical circuit may be connected to the battery (130), which may be situated inside the encasement (118) or handle, and the button (131) via the posterior connection (110) of the sheath. The exterior of the sheath (or portions thereof) may be conductive, thus completing the second arm of the electrical circuit. When the electrocautery/electrosurgery button (131) is pressed, current flows through the circuit from the outside of the sheath to the needle tip (103), resulting in localized electrocoagulation. One skilled in the art may configure connections from an external power source, and by-pass the need for a battery.

Referring to FIG. 23, an alternative motor drive may provide a mechanical force needed to move the sheath and rotate the needle, a connection to radiofrequency (RF) electrical source for electrosurgical cutting/coagulation, and a vacuum chamber at the back end of the needle for collecting cut tissue samples.

Referring to FIG. 24A, one embodiment of an encasement/handle (118) that may be used with the biopsy needle device can include a power switch, an electrosurgery connector, a toggle switch for extending and retracting the sheath, and a trigger for delivering RF energy for electrosurgical cutting and cauterization. In another embodiment, FIG. 21B shows the handle (118) with indicator lights and rocker switch controlling extension and retraction of the sheath.

Figure 25A:
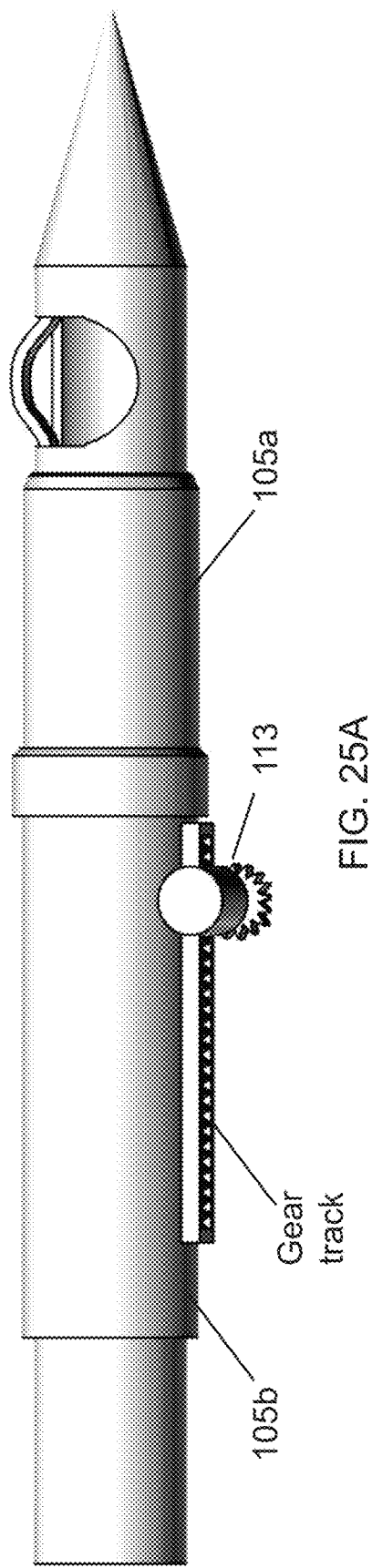
FIGS. 25A-25C show the sheath with gear and motor drive over the needle as an alternative way to retract the sheath. Luer lock can connect a distal sheath to a proximal sheath.
Figure 25B:
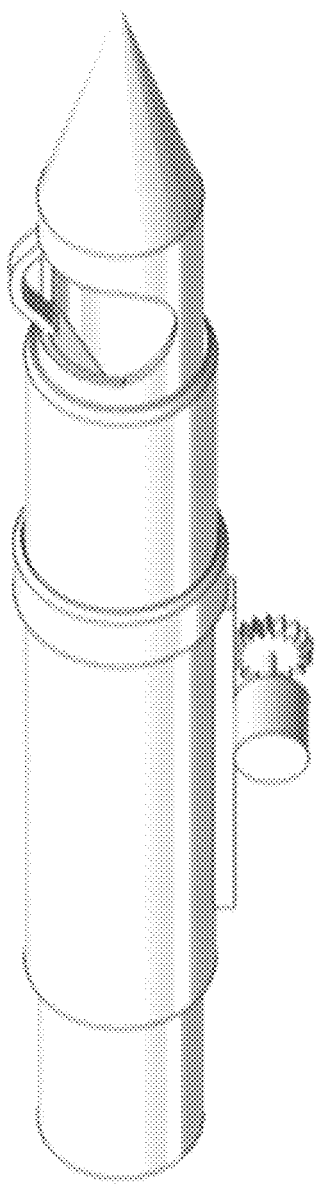
Figure 25C:
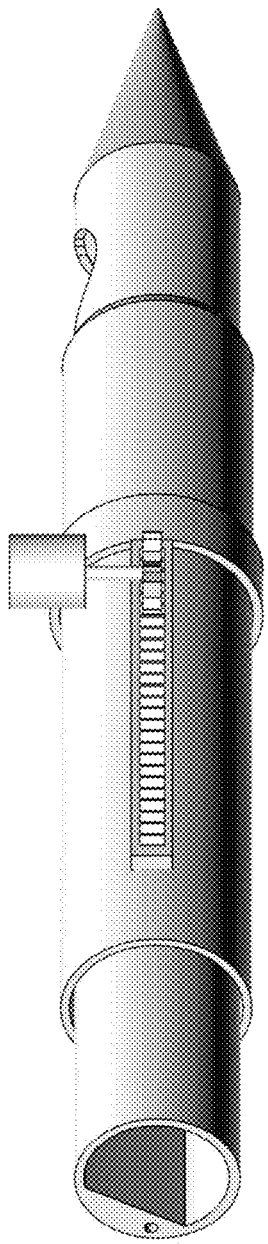

An alternative mechanism to retract the sheath in shown in FIGS. 25A-25C. In some embodiments, the sheath (105) may have a track disposed on its exterior surface. A gear (113) operatively coupled to a motor drive engages the track on the sheath, thereby causing translational movement of the sheath over the needle. In other embodiments, a Luer lock may connect a distal sheath (105a) to proximal sheath (105b).

Bio-Impedance

With electrification of the needle, additional uses of electricity beyond the control of bleeding are enabled. According to some embodiments, instead of having a single electrode, the needle system may further comprise multiple electrodes incorporated into an outer aspect, such as the sheath/cannula, of a percutaneous needle device or on the percutaneous needle itself. The geometry of these electrodes determine the spatial information provided for guidance of needle-based, percutaneous procedures. In a non-limiting embodiment, the needle system of the present invention makes use of both the spatial information provided by the needle and also the relative low bioimpedance of electrolyte-rich blood as a means to direct current flow and resultant electrical coagulation in case of a bleeding complication.

Referring now to FIGS. 27B to 33F, according to some embodiments, the present invention features a bio-impedance guided needle system (100). The system comprises a needle (101) having a tip (103) disposed at a distal end of the needle (101) for insertion into tissue, an optional outer sheath (105) slidably disposed around an exterior surface of the needle (101), and a plurality of electrodes (164) disposed on the needle (101), on a surface of the optional outer sheath, or both. In some embodiments, the sheath (105) is adapted to move between an open position away from the needle tip (103) such that at least a portion of the needle is exposed, and a closed position where said needle portion is covered by the sheath (105). In some embodiments, the plurality of electrodes (164) is configured to apply electrical current for cauterizing tissue, coagulating blood, obtaining multiple bio-impedance measurements to guide needle insertion and positioning, or initiating electron-dependent biochemical processes.

While bio-impedance may be implemented with a biopsy needle, this feature is not limited to biopsy needles and procedures. For instance, in other embodiments, bio-impedance may be used with needles in an ablation procedure. As known to one of ordinary skill in the art, ablation is a procedure involving the application of energy to destroy tissue. Thus, without deviating from the scope of the present invention, bio-impedance may be used with any needle or procedure in which guidance of the needle and knowledge of the needle's position is desired.

Accordingly, in some embodiments, the present invention provides a method of guiding insertion of a needle (101) into a subject. The subject may be a human or other mammal such as a dog, cat, horse, etc. For example, the subject may be a medical or veterinary patient. In one embodiment, the method may comprise providing a bio-impedance guided needle system (100) as described herein, obtaining multiple bio-impedance measurements from the plurality of electrodes (164), and determining directional information and/or position of the needle based on the multiple bio-impedance measurements. For example, the directional information and/or position of the needle can be determined by isolating or summing the various electrodes relative to other electrodes.

In one embodiment, the plurality of electrodes (164) comprises about 3-128 electrodes that are electrically capable yet isolatable from the other electrodes. In conjunction with the other embodiments, the needle (101) may also function as an additional electrode. In further embodiments, an insulating material may be partially covering the electrodes, a portion of the needle, or both. In some embodiments, the plurality of electrodes (164) comprises conductive strips, ribbons, or wires disposed axially along the surface of the outer sheath, the needle surface, or embedded and fixed within the needle. In other embodiments, the plurality of electrodes (164) comprises multiple concentric telescoping tubes each with an electrically-active exposed tip.

Figure 27A:
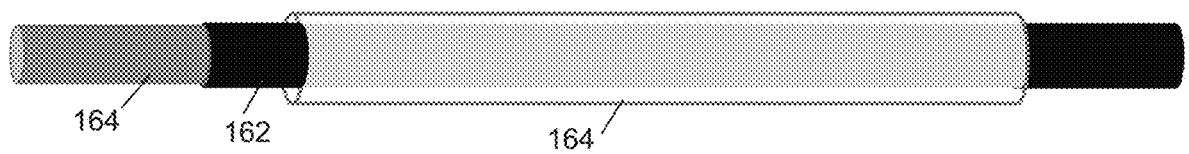
FIG. 27A shows an embodiment of the biopsy needle with the outer sheath/cannula acting as a single electrode, and the inner needle as the second electrode. Front and back details have been omitted for simplicity.
Figure 27B:
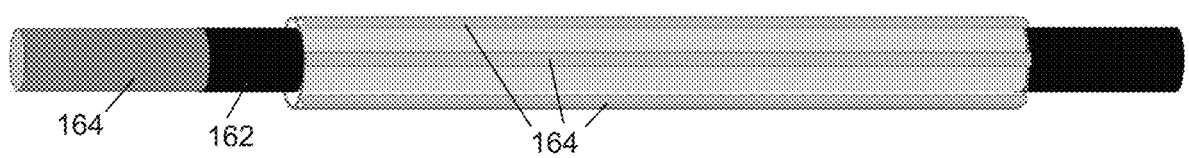
FIGS. 27B-27E show non-limiting embodiments of the outer sheath with multiple electrodes.
Figure 27C:
Figure 27D:
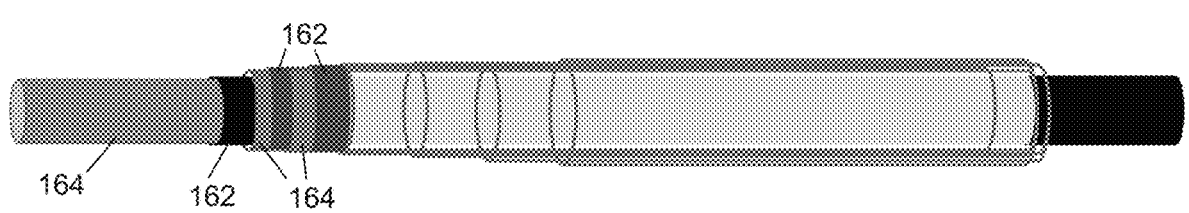
Figure 27E:
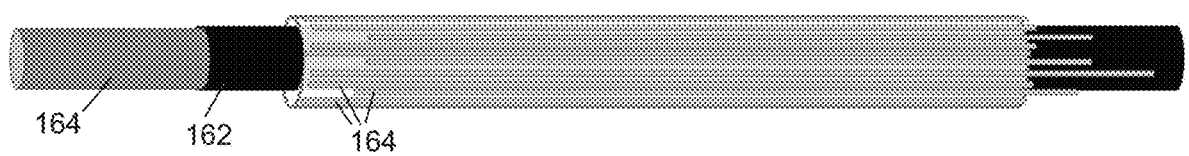

FIG. 27A shows an embodiment of a needle that may be used for electrocautery, but does not provide for bio-impedance guided insertion. In contrast, FIGS. 27B-27E show various embodiments of the needle having multiple electrodes that can provide bio-impedance guided insertion. These embodiments are examples of the electrodes placed on the outer sheath. The exposed inner needle can also act as another electrode whereas the black portion is coated with a dielectric or insulating material. In FIG. 27C, the needle had overlapping, partially-insulated plates making up the outer sheath/guide needle and serving as multiple additional electrodes to guide placement and/or where electricity should be deposited for electrocoagulation. FIG. 27D shows another non-limiting embodiment of multiple concentric overlapping cores with electrically-active exposed tips as multiple additional electrodes to guide where electricity should be deposited for safer electrocoagulation. FIG. 27E is yet another embodiment of a wire-enclosed guide needle, with multiple wires serving as additional electrodes. The front and back end connection details have been omitted for simplicity.

Figure 28A:
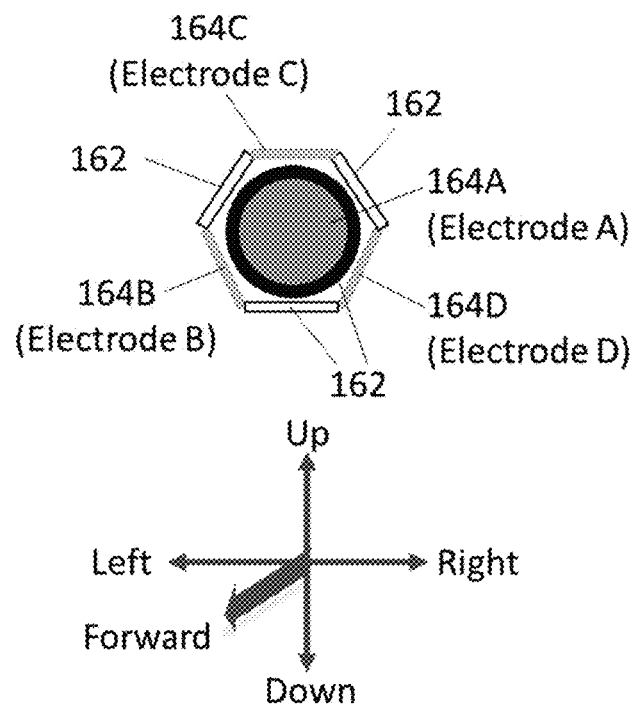
FIG. 28A is a cross-sectional view of the biopsy needle with three electrodes and dielectric material around the inner needle/electrode. Directional information can be obtained by isolating or summing the various electrodes relative to others.
Figure 28B:
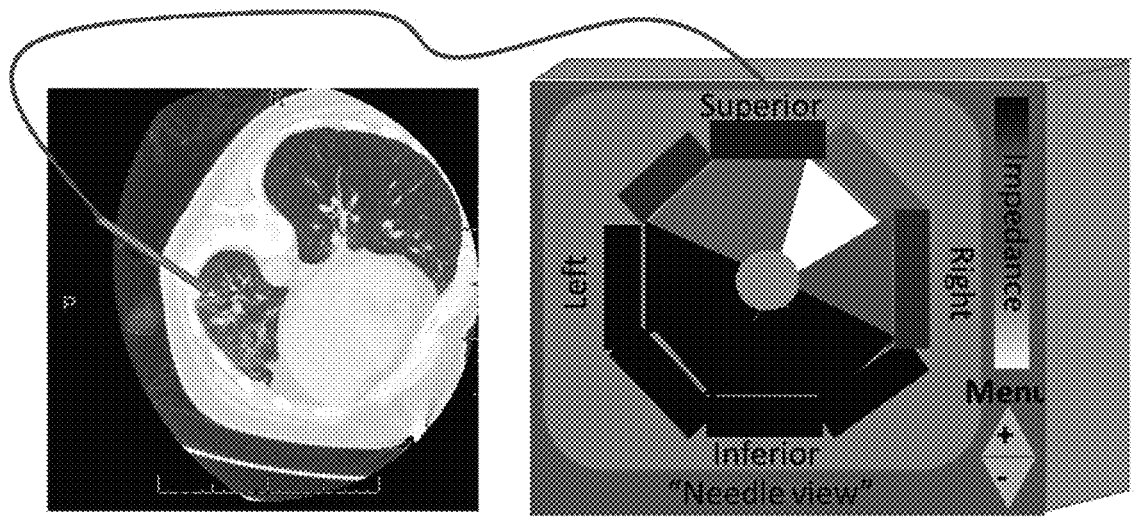
FIG. 28B shows the biopsy needle implementing bio-impedance to provide positional guidance of the needle complementary to external imaging guidance.
Figure 29:
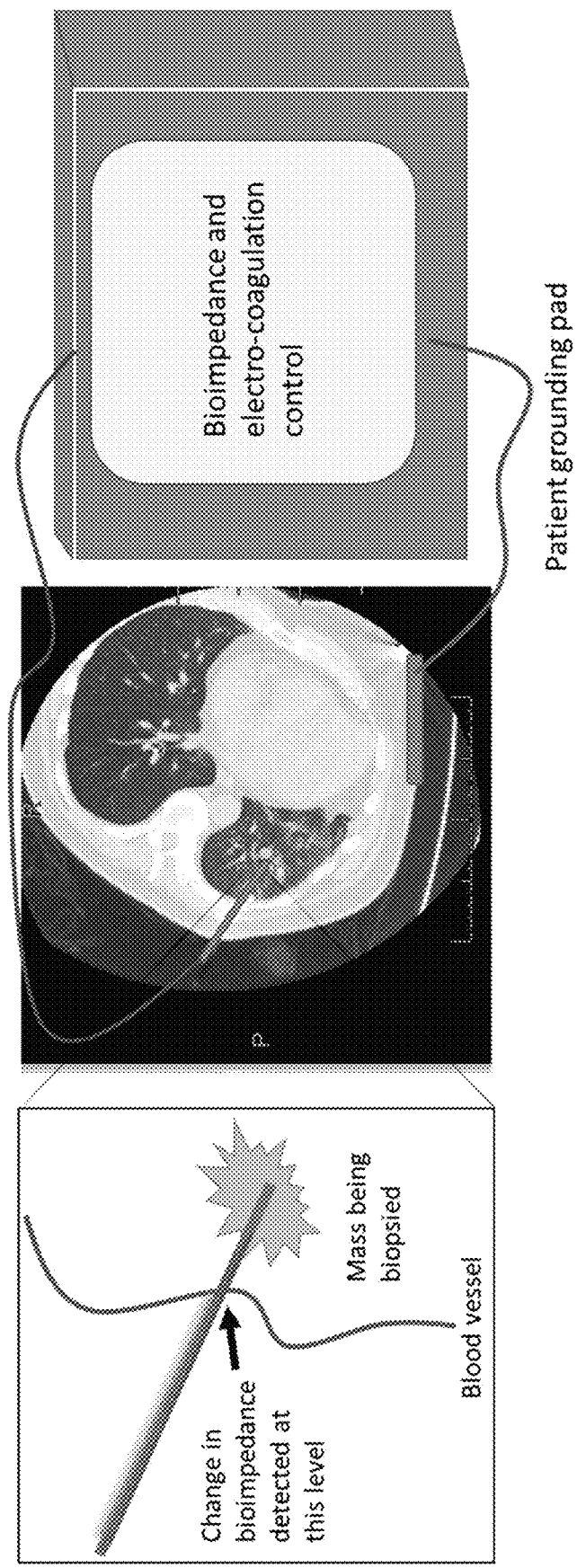
FIG. 29 show the use of real-time bioimpedance feedback to locate where the needle is in contact with blood and where to deliver electrocautery to address bleeding.
Figure 30A:
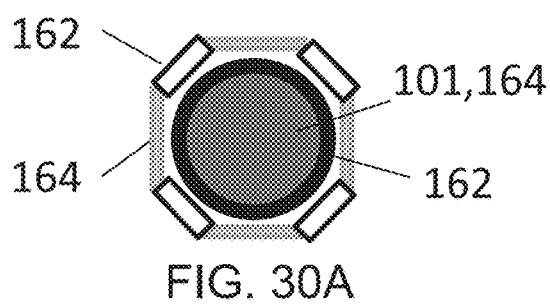
FIGS. 30A-30E are cross-sectional views showing non-limiting embodiments of the biopsy needle with multiple electrodes and dielectric material around the inner needle/electrode.
Figure 30B:
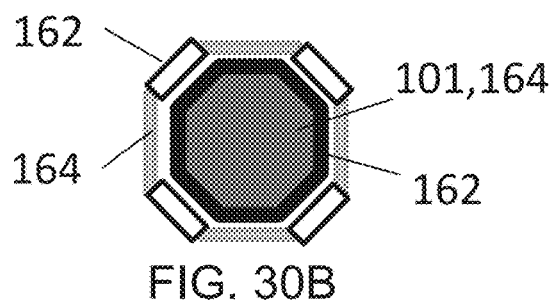
Figure 30C:
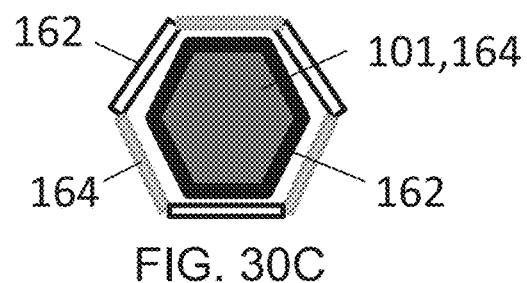
Figure 30D:
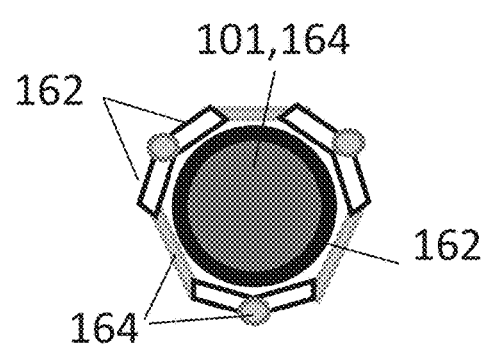
Figure 30E:
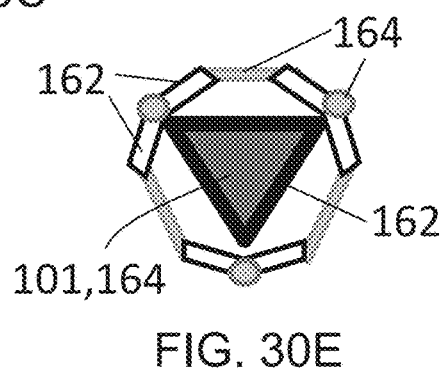
Figure 31A:
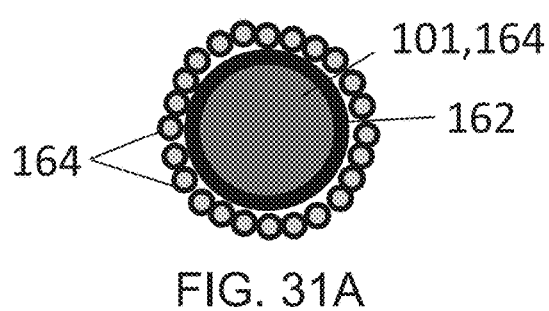
FIGS. 31A-31D are cross-sectional views of other non-limiting embodiments of the biopsy needle with multiple electrodes and dielectric material around the inner needle/electrode.
Figure 31B:
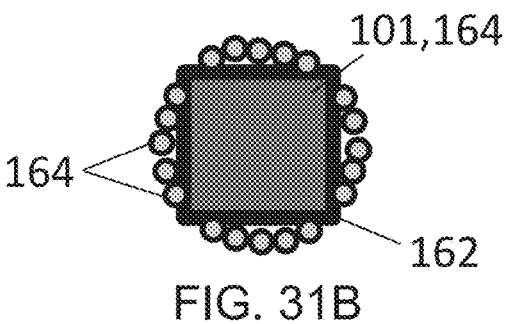
Figure 31C:
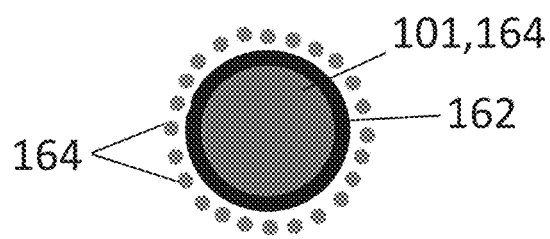
Figure 31D:
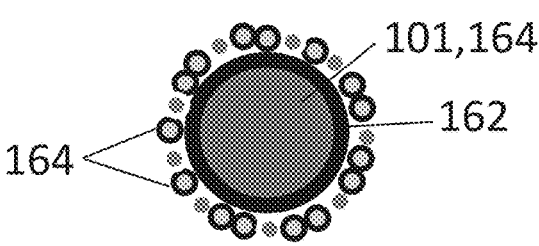
Figure 32A:
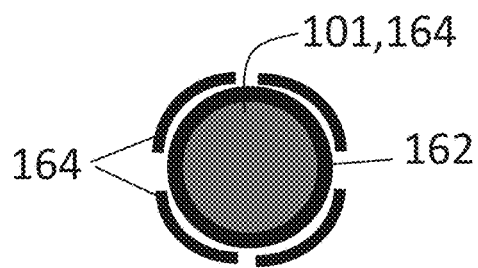
FIGS. 32A-32D are cross-sectional views of various non-limiting embodiments of the biopsy needle with multiple electrodes and dielectric material around the inner needle/electrode.
Figure 32B:
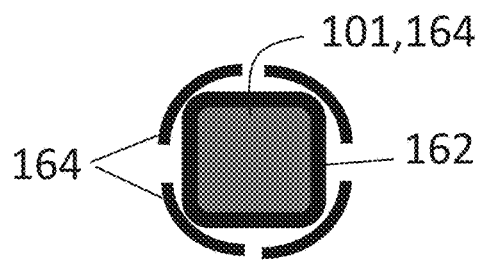
Figure 32C:
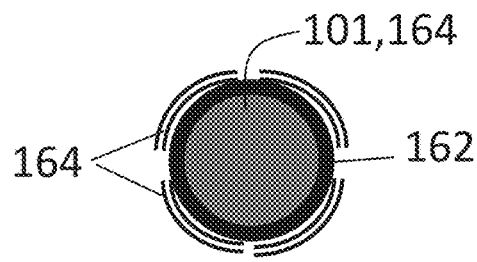
Figure 32D:
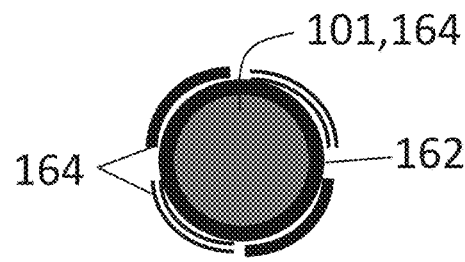

FIG. 28A shows an embodiment of the needle, in a cross-sectional view, with three electrodes and dielectric material around the inner needle/electrode. Referring to the table, in some embodiments, the resultant directional information can be obtained by isolating or summing the various electrodes relative to other electrodes. In preferred embodiments, the present invention may be used to provide positional guidance to a display box, as shown in FIG. 28B. This bioimpedance directionality may complement in real-time the snap-shots of information obtained during successive external image guidance (e.g. CT) scans to guide the needle.

In other preferred embodiments, the present invention may be used to provide real-time bioimpedance feedback on where the needle is in contact with blood and where to deliver electrocautery to address bleeding. As shown in FIG. 30, the left-most image is a close-up view of the needle damaging a blood vessel during a CT-guided lung biopsy as demonstrated in the middle image. A change in impedance is detected between blood and tissue. External grounding (optional) to the control and display box can improve the bioimpedance signal-noise and provide more focused electrocoagulation of the damaged blood vessel to prevent bleeding complications.

FIGS. 30A-30E show alternative embodiments of the arrangement of the electrodes around the inner needle. Of note, the inner needle may be entirely hollow, but it may also be partially hollow or completely solid depending on the clinical application (e.g. aspiration, biopsy, ablation, etc.). In some embodiments, the electrodes can have varying dielectric insulation along the shaft of the needle or the outer sheath. As shown in FIGS. 31A-31D, alternative embodiments of the needle may include wires that can each serve as an electrode with varying degrees of electrical exposure towards the tip. In some embodiments, the wires may be fully coated, partially coated, or completely uncoated. Referring to FIGS. 32A-32D, in some embodiments, the needle may have ribbons disposed on the outer sheath. These ribbons can serve as electrodes with varying degrees of electrical exposure towards the tip. In some embodiments, the ribbons may be fully coated, partially coated, or completely uncoated.

Figure 33A:
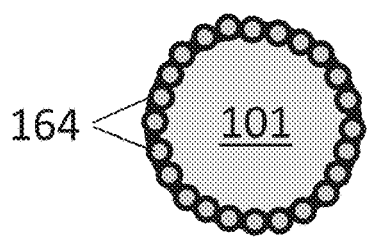
FIGS. 33A-33F are cross-sectional views of alternative embodiments of the needle with multiple electrodes embedded in the semi-solid or solid needle.
Figure 33B:
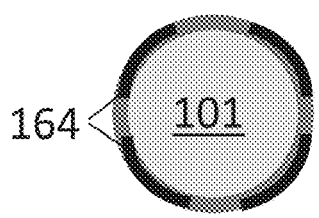
Figure 33C:
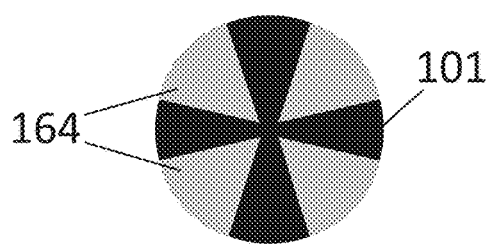
Figure 33D:
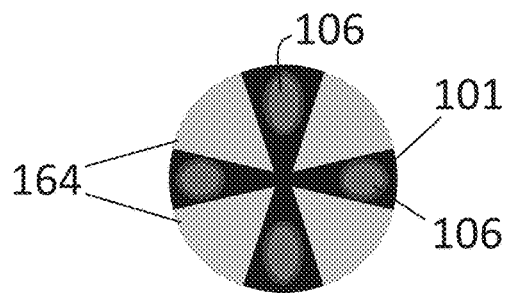
Figure 33E:
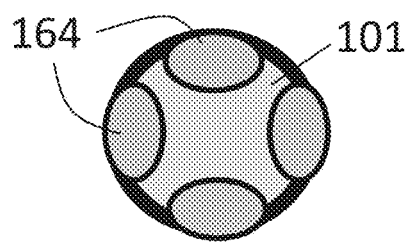
Figure 33F:
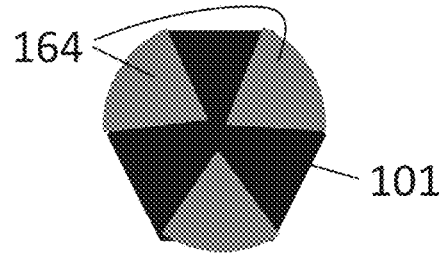

FIGS. 33A-33B show alternative embodiments of the needle where non-removable electrodes are incorporated into the outer surface of the inner needle. In these embodiments, the needle may have an outer sheath, or alternatively, no outer sheath. If the needle has an outer sheath, the outer sheath may have electrodes, or alternatively, no electrodes disposed thereon. In some embodiments, the inner needle may be entirely hollow, but it may also be partially hollow or completely solid. For example, the inner needle may have a lumen or no lumen depending on the specific clinical use (e.g. thermal cooling after ablation, aspiration, etc.). FIGS. 33C-33F show non-limiting embodiments incorporating the conductive surfaces into the substance of the needle shaft. For instance, multiple isolated but conductive faces can be incorporated into a solid needle. The solid needle may have lumens (e.g. for coolant for thermal applications, for aspiration/injection, etc.) or no lumen. Various embodiments of biopsy needle may feature a circular cross-section, or a non-circular or non-rounded cross-section. As shown in the figures, non-limiting examples of the needle cross-section include a square or rectangle, a triangle, or a polygon.

In some embodiments, a plurality of electrodes may be disposed axially on the surface of the outer sheath or needle. In alternative embodiments, as shown in FIG. 27D, the plurality of electrodes may be disposed radially, e.g. concentric, on the surface of the outer sheath or needle. In preferred embodiments, the needle may have two or more electrodes. Without wishing to be bound to a particular theory, the plurality of electrodes can provide better or more accurate directional information.

As has been described, the electrodes can be placed on an outer sheath of the needle, on the needle's surface, or embedded within the needle. With any of these configurations, the directional information of the needle can be obtained by isolating or summing the various electrodes relative to other electrodes.

Although multiple electrodes can be placed within the needle or on the surface of the needle or sheath, the overall diameter remains small, thereby reducing pain when the needle is inserted into a patient. For instance, the diameter at the thickest point may be less than 5 mm or about 7 gauge or higher. In some preferred embodiments, the diameter is less than 1.6 mm or about 16 gauge or higher. In other preferred embodiments, the diameter is less than 1 mm or about 20 gauge or higher.

EXAMPLES

The following are non-limiting examples of utilizing the systems of the present invention in a biopsy procedure. It is to be understood that the invention is not limited to the examples that will be described herein. Equivalents or substitutes are within the scope of the invention.

Example 1

Figure 26A:
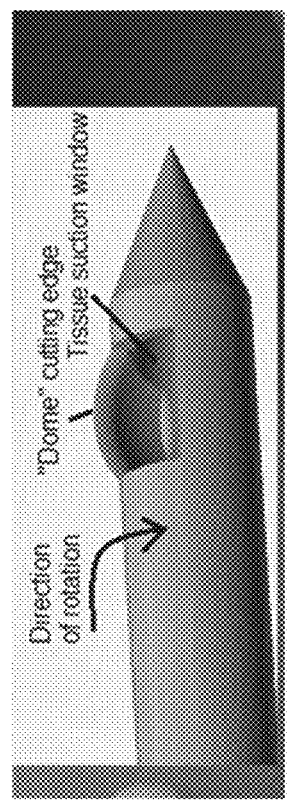

A non-limiting example of the biopsy needle device prototype of the present invention, herein referred to as the Triopsy needle, is shown in the top image of FIG. 26A. The inset provides the details of the 3D prototype. The 3D printed Triopsy needle is attached to a syringe after having aspirated a tofu-tissue model. The bottom image of FIG. 26A shows an exact-sized hollow needle without the dome, which is a model of standard full-core biopsy needles. FIG. 26B shows the result of 4 trials with the various biopsy needle types having been inserted equal depths and spun 5 times clockwise under different relative vacuum pressures. Significantly more tissue was harvested using the novel Triopsy-type needle (two-tailed paired t-test $p<0.01$). Data are presented as means and standard errors. Linear correlation ($R^2>0.9$, $p<0.01$) between mm of model tissue aspirated into the tubing and dry weight of the harvested tissue not shown.

FIG. 26C shows a theoretical comparison of amount of tissue harvested using current industry standard biopsy needles and using the Triopsy system of the present invention. The calculations are based on the assumption that current standard needles result in volume determined by the equation: $V=\pi r^2 \ast h$, where "r" is the radius of tissue and "h" is the height of the sheath. For the present invention, the volume is calculated using the equation: $V=\pi r^2 \ast 2\pi R \ast n$, where "r" is the radius of the inner core, "R" is the outer radius of the coil of tissue, and "n" is the number of coils. In this comparison, the outer coil radius (R) was set equal to the inner core of tissue radius for both this system and the standard for comparison (r), and the number of coils (n) was set as the diameter of the tissue divided into a fixed 15 mm, which was arbitrarily set as the core height (h).

Example 2: Biopsy Procedure

The biopsy needle includes a sheath through which biopsy device and other accessories can be inserted. Accessories include electrocautery device, radioopaque marker insertion device, tissue sealant injector, device to inject filler material, etc.
1. Prepare device: use syringe to apply suction; turn stopcock to preserve vacuum.
2. Use ultrasound guidance to advance needle/outer sheath into patient and position at distal end of tumor.
3. Use mechanics to retract outer sheath to expose expandable curved cutting blade and needle lumen.
4. Use stopcock to apply vacuum to needle lumen.
5. Rotate device to collect tissue biopsy (manual, motor driven, spring driven).
6. Stop rotation and reposition outer sheath.
7. Collect biopsy using vacuum and store in collection chamber
8. Use stopcock to close vacuum
9. Disengage outer sheath (luer adapter) from biopsy needle unit, if desired
10. Remove needle unit; sheath (optionally) remains in place Example 3: Biopsy Procedure with Electrocautery Device 1. Apply electrode pad to patient body and connect to electrocautery unit.
2. Connect electrocautery unit to biopsy device.
3. Insert electrocautery device into sheath and engage using luer adapter.
4. Advance electrocautery device tip into biopsy site.
5. Push activation button and hold to use electrocautery.
6. Rotate needle (mechanical, motor, or spring) while pulling the device towards the operator (or towards the entry site or through the tumor).
7. Release activation button to inactivate electrocautery.
8. Disengage sheath from electrocautery unit.
9. Remove electrocautery unit.
10. Remove sheath.

Example 3: Biopsy Procedure Triopsy Edge Complex Device

1. Apply grounding pad to patient and attach to electrocautery unit. Attach electrocautery unit to biopsy device.
2. Insert needle and sheath into patient under external imaging (e.g. ultrasound) visualization.
3. Position within the tumor, preferably distally for pullback biopsy.
4. Press start button to activate device. Solid green ready light appears.
5. Press start button to begin biopsy process. Green light begins to blink.

6. Outer sheath retracts.
7. Vacuum starts.
8. Electrosurgery signal directed to cutting blade.
9. Needle begins to rotate for n rotations (n=1-20).
10. Electrosurgery inactivated.
11. Outer sheath extends distally.
12. Vacuum continues to collect tissue.
13. Vacuum turns off.
14. Solid green light reappears-ready light.
15. Reposition biopsy device to starting position.
16. Depress and hold button to activate electrocautery.
17. Inactivate biopsy parts.
18. Withdraw outer sheath to expose electrocautery.
19. Blinking red light is activated, green light off.
20. Physician moves needle/sheath outward to cauterize biopsy tract.
21. Release button to stop electrocautery unit.
22. Blinking red light is inactivated.
23. Outer sheath advanced distally.
24. Electrocautery unit shuts down.

The disclosures of the following U.S. patents are incorporated in their entirety by reference herein: U.S. Pat. Application No. 2002/0026188.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawing. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A biopsy system (100) for harvesting a target tissue, comprising:
   a. a needle (101) having a tip (103) disposed at a distal end of the needle (101) for insertion into tissue, wherein a lumen (106) is disposed in the needle (101);
   b. an aperture (102) disposed at or near the distal end of the needle, said aperture (102) fluidly connected to the lumen (106); and
   c. a cutting mechanism (104) comprising an expandable dome-shape, semispherical structure having an edge adapted to cut tissue, said cutting mechanism (104) having at least a portion thereof disposed in or over the aperture (102);
   d. a sheath (105) slidably disposed around an exterior surface of the needle (101), the sheath (105) adapted to move between at least an open position where the aperture (102) and cutting mechanism (104) are exposed, and a closed position where the aperture (102) and cutting mechanism (104) are covered by the sheath (105);
   e. a sealing mechanism for cauterizing tissue that contacts said sealing mechanism, coagulating said tissue, or a combination thereof; and
   f. a mechanism for rotating the needle;
   wherein when the needle (101) is inserted into the target tissue, the sheath (105) deployed in the open position, and the needle (101) rotated via the rotation mechanism, the cutting mechanism (104) cuts the tissue and directs said cut tissue into the aperture (102) and further into the lumen (106), while contacting tissue is sealed by the sealing mechanism.

2. The system (100) of claim 1, wherein the cutting mechanism (104) is deployable, said deployable cutting mechanism (104) having at least a portion thereof disposed in or over the aperture (102), said deployable cutting mechanism (104) adapted to move between an extended position where said portion projects from the needle (101), and a retracted position (120) where said portion is not projecting from the aperture (102), wherein when the needle (101) is inserted into the target tissue and the sheath (105) is moved to the open position, the deployable cutting mechanism (104) projects out from the aperture (102) and into the extended position.

3. The system (100) of claim 1, wherein the needle tip (103) or cutting mechanism (104) is removable from the needle, wherein the removed tip or cutting mechanism is adapted to function as a tissue biopsy marker or wire localizer for indicating a location of the biopsied tissue.

4. The system (100) of claim 1, wherein a gear (113) is operatively coupled to the sheath (105) and a motor for moving the sheath between the open position and the closed position.

5. The system (100) of claim 1, wherein the lumen (106) is under negative pressure to allow the cut tissue to collect in the lumen (106), wherein the negative pressure in the lumen is generated using suction or a vacuum source.

6. The system (100) of claim 1, wherein the sealing mechanism is an electrocautery system operatively connected to the cutting mechanism (104), wherein when the electrocautery system is activated, and the cutting mechanism (104) is activated to provide cauterization to contacting tissue.

7. The system (100) of claim 1, wherein the sealing mechanism comprises a cauterizing surface, wherein the cauterizing surface is the needle tip (103) which acts as an exposed anode, and a shaft of the needle acts as a cathode, wherein the cauterizing mechanism further comprises an insulator that protects the cut tissue from being cauterized.

8. The system (100) of claim 1 further comprising at least one additional lumen (106) for holding or administering a solution.

9. The system (100) of claim 1 further comprising a tissue collection chamber fluidly coupled to the needle lumen (106) for storing the cut tissue.

10. The system (100) of claim 1 further comprising a plurality of electrodes (164) disposed on a surface of the sheath, on the needle, or both, wherein the plurality of electrodes is configured to apply electrical current for cauterizing tissue, coagulating blood, obtaining multiple bio-impedance measurements to guide needle insertion and positioning, or initiating electron-dependent biochemical processes.

11. A method of harvesting tissue, said method comprising:
 a. providing a biopsy system (100) according to claim 1;
 b. inserting the needle (101), starting with the tip (103), into a tissue of concern;
 c. retracting the sheath (105) to expose the cutting mechanism (104);
 d. rotating the needle (101) and applying suction to the lumen, thereby cutting the tissue with the cutting mechanism (104) and sealing contacting tissue via the sealing mechanism, wherein the cut tissue is directed into the lumen (150).

12. A biopsy system (100) for harvesting a target tissue, comprising:
 a. a needle (101) having a tip (103) disposed at a distal end of the needle (101) for insertion into tissue, wherein a lumen (106) is disposed in the needle (101);
 b. an aperture (102) disposed at or near the distal end of the needle, said aperture (102) fluidly connected to the lumen (106); and
 c. a cutting mechanism (104) comprising an expandable semisphere-shape structure having an edge adapted to cut tissue, said cutting mechanism (104) having at least a portion thereof disposed in or over the aperture (102);
 d. a sheath (105) slidably disposed around an exterior surface of the needle (101), the sheath (105) adapted to move between at least an open position where the aperture (102) and cutting mechanism (104) are exposed, and a closed position where the aperture (102) and cutting mechanism (104) are covered by the sheath (105);
 e. a sealing mechanism for cauterizing tissue that contacts said sealing mechanism, coagulating said tissue, or a combination thereof;
 f. a mechanism for rotating the needle; and
 g. a mechanism for retracting the needle;
 wherein when harvesting the target tissue, the needle (101) is inserted into the target tissue, the sheath (105) is deployed in the open position, the needle (101) is rotated via the rotation mechanism and simultaneously retracted via the retraction mechanism, wherein as the needle is rotating and simultaneously being retracted, the cutting mechanism (104) cuts the tissue and directs said cut tissue into the aperture (102) and further into the lumen (106), while contacting tissue is sealed by the sealing mechanism.

13. A biopsy system (100) for harvesting a target tissue, comprising:
 a. a needle (101) having a tip (103) disposed at a distal end of the needle (101) for insertion into tissue, wherein a lumen (106) is disposed in the needle (101);
 b. an aperture (102) disposed at or near the distal end of the needle, said aperture (102) fluidly connected to the lumen (106); and
 c. a cutting mechanism (104) adapted to cut tissue, said cutting mechanism (104) having at least a portion thereof disposed in or over the aperture (102);
 d. a sheath (105) slidably disposed around an exterior surface of the needle (101), the sheath (105) adapted to move between at least an open position where the aperture (102) and cutting mechanism (104) are exposed, and a closed position where the aperture (102) and cutting mechanism (104) are covered by the sheath (105);
 e. a sealing mechanism for cauterizing tissue that contacts said sealing mechanism, coagulating said tissue, or a combination thereof;
 f. a mechanism for rotating the needle; and
 g. a mechanism for retracting the needle;
 wherein when harvesting the target tissue, the needle (101) is inserted into the target tissue, the sheath (105) is deployed in the open position, the needle (101) is rotated via the rotation mechanism and simultaneously retracted via the retraction mechanism, wherein as the needle is rotating and simultaneously being retracted, the cutting mechanism (104) cuts the tissue and directs said cut tissue into the aperture (102) and further into the lumen (106), while contacting tissue is sealed by the sealing mechanism.

14. The system (100) of claim 13, wherein the cutting mechanism (104) is deployable, said deployable cutting mechanism (104) having at least a portion thereof disposed in or over the aperture (102), said deployable cutting mechanism (104) adapted to move between an extended position where said portion projects from the needle (101), and a retracted position (120) where said portion is not projecting from the aperture (102), wherein when the needle (101) is inserted into the target tissue and the sheath (105) is moved to the open position, the deployable cutting mechanism (104) projects out from the aperture (102) and into the extended position.

15. The system (100) of claim 13, wherein a gear (113) is operatively coupled to the sheath (105) and a motor for moving the sheath between the open position and the closed position.

16. The system (100) of claim 13, wherein the lumen (106) is under negative pressure to allow the cut tissue to collect in the lumen (106), wherein the negative pressure in the lumen is generated using suction or a vacuum source.

17. The system (100) of claim 13 further comprising at least one additional lumen (106) for holding or administering a solution.

18. The system (100) of claim 13 further comprising a tissue collection chamber fluidly coupled to the needle lumen (106) for storing the cut tissue.

19. The system (100) of claim 13 further comprising a plurality of electrodes (164) disposed on a surface of the sheath, on the needle, or both, wherein the plurality of electrodes is configured to apply electrical current for cauterizing tissue, coagulating blood, obtaining multiple bioimpedance measurements to guide needle insertion and positioning, or initiating electron-dependent biochemical processes.

20. A method of harvesting tissue, said method comprising:
 a. providing a biopsy system (100) according to claim 13;
 b. inserting the needle (101), starting with the tip (103), into a tissue of concern;
 c. retracting the sheath (105) to expose the cutting mechanism (104);
 d. applying suction to the lumen;
 e. simultaneously rotating and retracting the needle (101), thereby cutting the tissue with the cutting mechanism (104) and sealing contacting tissue via the sealing mechanism, wherein the cut tissue is directed into the lumen (150).

* * * * *